US012569361B2

(12) United States Patent
Holman et al.

(10) Patent No.: US 12,569,361 B2
(45) Date of Patent: Mar. 10, 2026

(54) DEVICES AND METHODS TO TREAT AND PREVENT DIVERTICULITIS

(71) Applicant: GYRUS ACMI, INC., Southborough, MA (US)

(72) Inventors: Thomas J. Holman, Princeton, MN (US); Nikhil M. Murdeshwar, Maple Grove, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 817 days.

(21) Appl. No.: 17/185,610

(22) Filed: Feb. 25, 2021

(65) Prior Publication Data

US 2021/0259865 A1 Aug. 26, 2021

Related U.S. Application Data

(60) Provisional application No. 63/116,681, filed on Nov. 20, 2020, provisional application No. 62/981,369, filed on Feb. 25, 2020.

(51) Int. Cl.
*A61F 2/962* (2013.01)
*A61B 17/00* (2006.01)
(Continued)

(52) U.S. Cl.
CPC ........ *A61F 2/962* (2013.01); *A61B 17/00234* (2013.01); *A61F 2/82* (2013.01);
(Continued)

(58) Field of Classification Search
CPC ............ A61B 17/062; A61B 17/00491; A61B 2017/00805; A61B 2017/00495; A61B 2017/348; A61B 2017/3482; A61B 2017/3484; A61B 2017/3486; A61B 17/3415; A61B 17/34; A61B 17/3421;
(Continued)

(56) References Cited

U.S. PATENT DOCUMENTS 5,100,419 A 3/1992 Ehlers
6,086,585 A * 7/2000 Hovda ............... A61B 18/1402
606/41

(Continued)

FOREIGN PATENT DOCUMENTS

EP 1880686 B1 6/2017

OTHER PUBLICATIONS

"U.S. Appl. No. 17/185,592, Examiner Interview Summary mailed Mar. 4, 2024", 2 pgs.

(Continued)

*Primary Examiner* — Brooke Labranche
*Assistant Examiner* — Rachael L Geiger
(74) *Attorney, Agent, or Firm* — Schwegman Lundberg & Woessner, P.A.

(57) ABSTRACT

A method of treating diverticulitis and the diverticulum by reducing the bioactivity of the diverticulum such that the diverticulum necroses. The devices and methods include placing an endoscopic device within a colonic lumen relative to at least one diverticulum and inverting the diverticulum. Once inverted, the diverticulum is collapsed and sealed. Overtime, the inverted diverticulum will necrose and be absorbed by the body or slough off and be expelled.

14 Claims, 19 Drawing Sheets

(51) Int. Cl.

| | |
|---|---|
| *A61B 17/12* | (2006.01) |
| *A61B 18/00* | (2006.01) |
| *A61F 2/82* | (2013.01) |
| *A61F 2/95* | (2013.01) |
| *A61K 9/00* | (2006.01) |
| *A61K 9/16* | (2006.01) |
| *A61K 33/38* | (2006.01) |
| *A61K 45/06* | (2006.01) |
| *A61M 31/00* | (2006.01) |

(52) U.S. Cl.
CPC .............. *A61F 2/95* (2013.01); *A61K 9/0009* (2013.01); *A61K 9/0019* (2013.01); *A61K 9/1676* (2013.01); *A61K 33/38* (2013.01); *A61K 45/06* (2013.01); *A61M 31/00* (2013.01); *A61B 2017/00278* (2013.01); *A61B 2017/00818* (2013.01); *A61B 2017/12018* (2013.01); *A61B 2018/00291* (2013.01); *A61B 2018/00494* (2013.01); *A61B 2217/005* (2013.01); *A61B 2217/007* (2013.01); *A61F 2210/0014* (2013.01); *A61F 2210/0076* (2013.01); *A61F 2220/005* (2013.01); *A61M 2202/0007* (2013.01); *A61M 2202/06* (2013.01)

(58) Field of Classification Search
CPC ........ A61B 2017/3488; A61B 10/0233; A61B 2017/00349; A61B 17/12013; A61B 17/00234; A61B 2017/00575; A61B 2017/00818; A61B 17/04; A61B 2017/06176; A61B 17/1114; A61B 2017/00663; A61B 17/06166; A61B 2017/06052; A61B 2017/06057; A61B 2017/0641; A61B 1/31; A61B 17/0469; A61B 17/122; A61B 17/1285; A61B 2017/00296; A61B 17/0644; A61B 17/068; A61B 17/1227; A61B 18/1477; A61B 2017/3445; A61B 17/0487; A61B 17/08; A61B 17/221; A61B 2018/00267; A61B 2018/1425; A61B 2017/00641; A61B 1/00085; A61B 17/29; A61B 2017/303; A61B 2018/00494; A61M 5/32; A61M 25/0637; A61M 25/06; A61M 25/065; A61F 2/0036
See application file for complete search history.

(56) References Cited

U.S. PATENT DOCUMENTS

| | | | | |
|---|---|---|---|---|
| 6,425,854 B1 * | 7/2002 | Galt | ..................... | A61B 17/062 |
| | | | | 600/29 |
| 9,084,605 B2 * | 7/2015 | Hawkins | ........... | A61B 17/3421 |
| 9,955,974 B2 | 5/2018 | Adam | | |
| 12,109,136 B2 | 10/2024 | Murdeshwar et al. | | |
| 2004/0073247 A1 * | 4/2004 | Loshakove | ........... | A61B 17/11 |
| | | | | 606/184 |
| 2009/0117157 A1 * | 5/2009 | Brin | ......................... | A61P 7/10 |
| | | | | 424/190.1 |
| 2010/0015200 A1 * | 1/2010 | McClain | ................. | A61L 27/34 |
| | | | | 424/94.1 |
| 2011/0277777 A1 | 11/2011 | Alexander et al. | | |
| 2013/0158465 A1 | 6/2013 | Bates et al. | | |
| 2015/0209109 A1 | 7/2015 | Rege et al. | | |
| 2017/0079654 A1 * | 3/2017 | Malanowski | ........ | A61B 17/068 |
| 2021/0259864 A1 | 8/2021 | Murdeshwar et al. | | |

OTHER PUBLICATIONS

"U.S. Appl. No. 17/185,592, Non Final Office Action mailed Dec. 12, 2023", 10 pgs.

"U.S. Appl. No. 17/185,592, Notice of Allowance mailed Jun. 7, 2024", 9 pgs.

"U.S. Appl. No. 17/185,592, Response filed Mar. 12, 2024 to Non Final Office Action mailed Dec. 12, 2023", 12 pgs.

"U.S. Appl. No. 18/827,359, Preliminary Amendment filed Nov. 19, 2024", 5 pgs.

* cited by examiner

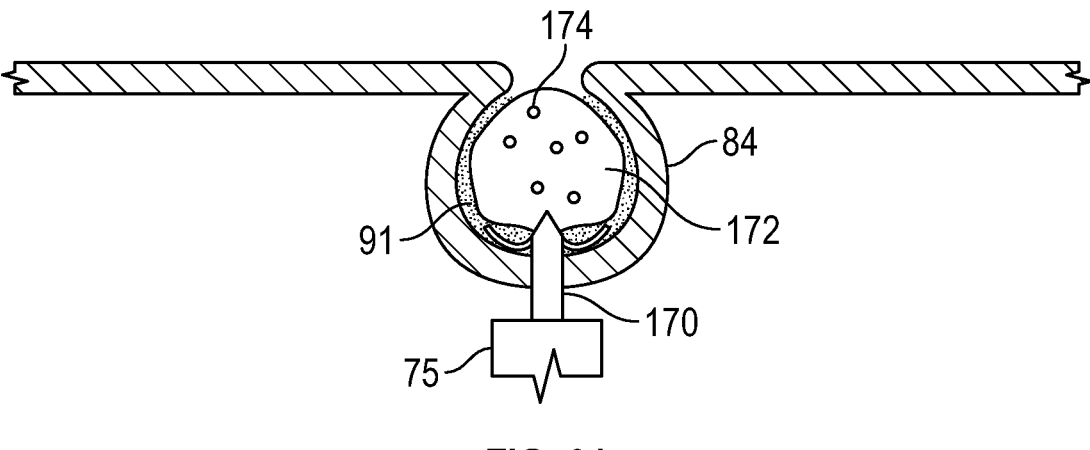
FIG. 31
FIG. 32
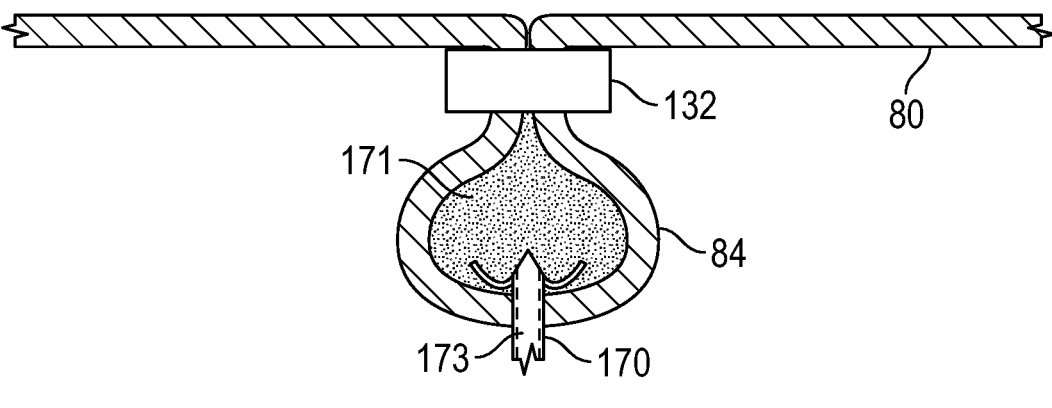
FIG. 33

DEVICES AND METHODS TO TREAT AND PREVENT DIVERTICULITIS

PRIORITY AND RELATED APPLICATIONS

This application claims the benefit of priority to U.S. Provisional Patent Application Ser. No. 63/116,681, titled, "DEVICES AND METHODS TO TREAT AND PREVENT DIVERTICULITIS", filed on Nov. 20, 2020 and to U.S. Provisional Patent Application Ser. No. 62/981,369, titled, "DEVICES AND METHODS TO TREAT AND PREVENT DIVERTICULITIS", filed Feb. 25, 2020, both of which are hereby incorporated by reference in their entirety.

TECHNICAL FIELD

This document pertains generally, but not by way of limitation, to devices, systems, and methods for the treatment of diverticulitis. More particularly, the disclosure relates to a device, system and method for treating and preventing the recurrence of diverticulitis.

BACKGROUND

Diverticulitis is caused by infection or inflammation of small pouches in the lining of the colon that bulge outward through weak spots. Such pouches are referred to as diverticula. Each pouch is called a diverticulum and pouches (plural) are called diverticula. Inflammation of the diverticula may lead to bleeding, infections, small tears, perforations, or blockages in the colon.

Diverticular disease results when at least one small pouch in the colon bulges outward through a weak spot. Many Americans over the age 40 have diverticulosis (i.e., the condition of having diverticula), and the condition becomes more common as people age. In many patients, diverticulosis remains asymptomatic. However, in some cases of diverticulosis, the pouches become infected or inflamed. When the pouches become infected or inflamed, the condition is called diverticulitis. This can happen in about 10 to 25 percent of people with diverticulosis. Most people with diverticulosis do not have any discomfort or symptoms. However, symptoms may include mild cramps, bloating, and constipation. The most common sign is tenderness around the left side of the lower abdomen. If infection is the cause, fever, nausea, vomiting, chills, cramping, and constipation may occur as well. The severity of symptoms depends on the extent of the infection and complications. Diverticulitis can lead to bleeding, infections, perforations or tears, or blockages. These complications always require treatment to prevent them from progressing and causing serious illness.

The infection causing diverticulitis can form an abscess in the colon. An abscess is an infected area with pus that may cause swelling and destroy tissue. Sometimes the infected diverticula may develop small holes, called perforations. These perforations allow pus to leak out of the colon into the abdominal area. If the abscess does not clear up with antibiotics, the doctor may need to drain it. To drain the abscess, the doctor uses a needle and a small tube called a catheter. The doctor inserts the needle through the skin and drains the fluid through the catheter. This procedure is called percutaneous catheter drainage. Sometimes surgery is needed to clean the abscess and, if necessary, remove part of the colon. A large abscess can become a serious problem if the infection leaks out and contaminates areas outside the colon. Infection that spreads into the abdominal cavity is called peritonitis. Peritonitis requires immediate surgery to clean the abdominal cavity and remove the damaged part of the colon. Without surgery, peritonitis can be fatal.

A fistula is an abnormal connection of tissue between two organs or between an organ and the skin. When damaged tissues come into contact with each other during infection, they sometimes stick together. If they heal that way, a fistula forms. When diverticulitis-related infection spreads outside the colon, the colon's tissue may stick to nearby tissues. The organs usually involved are the bladder, small intestine, and skin. The most common type of fistula occurs between the bladder and the colon. It affects men more than women. This type of fistula can result in a severe, long-lasting infection of the urinary tract. The problem can be corrected with surgery to remove the fistula and the affected part of the colon.

The scarring caused by infection may cause partial or total blockage of the large intestine. When this happens, the colon is unable to move bowel contents normally. When the obstruction totally blocks the intestine, emergency surgery is necessary. Partial blockage is not necessarily an emergency, so the surgery to correct it can be planned.

Current treatment for diverticulitis focuses on clearing up the infection and inflammation, resting the colon, and preventing or minimizing complications. An attack of diverticulitis without complications may respond to antibiotics within a few days if treated early enough. An acute attack with severe pain or severe infection may require a hospital stay. Most acute cases of diverticulitis are treated with antibiotics (oral or intravenous) and a liquid diet. If attacks are severe or frequent, the doctor may advise surgery. During surgery, the surgeon removes the affected part of the colon and joins the remaining sections. This type of surgery, called colon resection and anastomosis, aims to keep attacks from coming back and to prevent complications. The doctor may also recommend surgery for complications of a fistula or intestinal obstruction. If antibiotics do not correct an attack, emergency surgery may be required. Other reasons for emergency surgery include a large abscess, perforation, peritonitis, or continued bleeding.

Surgery usually involves two operations. The first surgery will clear the infected abdominal cavity and remove part of the colon. Because of infection and sometimes obstruction, it is not safe to rejoin the colon during the first operation. Instead, the surgeon creates a temporary hole, or stoma, in the abdomen. The end of the colon is connected to the hole, a procedure called a colostomy, to allow normal eating and bowel movements. The stool goes into a bag attached to the opening in the abdomen. In the second operation, the surgeon rejoins the ends of the colon. In some instances, rejoining the ends of the colon is not possible and the patient will require the colostomy bag for the rest of their lives.

Currently no reliable way exists to acutely treat diverticulitis, other than supportive measures, or urgent surgery in severe cases. Even for patients in whom symptoms spontaneously resolve (e.g., pain ceases), currently no reliable nonsurgical interventions can be employed to prevent recurrent symptoms. Therefore, a significant unmet medical need remains to develop nonsurgical, minimally invasive interventions that can prevent and treat diverticulitis.

Overview

The present inventors have recognized, among other things, that problems to be solved in treating diverticulitis include the lack of minimally invasive interventions that can treat and prevent diverticulitis. Current treatments include either medication (oral or intravenous) or, in the most extreme cases, surgery. In cases of uncomplicated diverticulitis, such as localized diverticular inflammation, treatment may include antibiotics to treat infections and dietary changes while the bowel heals. In cases of complicated diverticulitis, such as diverticular inflammation associated with an abscess, phlegmon, fistula, obstruction, bleeding, or perforation, treatment may include intravenous antibiotics as well as treatment of other issues such as drainage of an abdominal abscess, if one has formed. However, certain cases the treatment will require surgery. For example, surgery may be required for cases of complicated diverticulitis (such as a bowel abscess, fistula or obstruction, or a perforation in the bowel wall), patients having multiple episodes of uncomplicated diverticulitis, or other considerations (such as a patient with a weakened immune system). Some patients may undergo a rection and anastomosis, where the surgeon removes diseased segments (resection) of the intestine and then reconnects the healthy segments (anastomosis). If resection is not possible (i.e., there is too much inflammation that it is not possible to rejoin the colon and rectum), the surgeon will perform a colostomy.

In some treatments, the diverticulum is treated such that while the current infection is treated, the diverticulum is maintained. That is, the bioactivity of the diverticulum remains after treatment. In some instances, the treatment may call for removing the diverticulum. However, removing the diverticulum can present additional challenges because the risk of perforations. The present subject matter can provide solutions to this problem and other problems, such as by providing minimally invasive surgical implants, devices, and methods to treat and prevent diverticulitis and reduce the need that a patient may need to undergo surgery to treat diverticulitis.

In one example, a system for treating a diverticulum is provided. For example, an endoscopic device including a shaft configured to be deployed at a site adjacent to a diverticulum can used with a treatment device to invert and treat the diverticulum such that the diverticulum necroses. In one example, the diverticulum can be inverted and collapsed. In one example, the diverticulum can be inverted, collapsed, and sealed. For example, a band or stent can be placed around the inverted and collapsed diverticulum to support the diverticulum as the diverticulum necroses.

In one example, the treatment device can include a needle having a tip and at least one expandable arm, where the needle is configured to pierce the diverticulum and the at least one expandable arm configured to engage the diverticulum. Once engaged, the needle can be retracted to invert the diverticulum.

In on example, a method of treating a diverticulum can be provided. The method can include placing a working end of an endoscope device within a colonic lumen relative to a diverticulum, advancing a treatment device from the working end, the treatment device including: a first member configured to couple to the diverticulum, and a second member positioned within and configured to advance from the first member. The method can include advancing the first member until the first member is coupled to the diverticulum and retracting the first member to invert the diverticulum. Once inverted, the second member can be advanced into the inverted diverticulum to deliver a bioadhesive into the inverted diverticulum via the second member. The method can include collapsing the inverted diverticulum such that the inverted diverticulum is adhered to portion of itself and portions of the treatment device.

This overview is intended to provide an overview of subject matter of the present patent application. It is not intended to provide an exclusive or exhaustive explanation of the invention. The detailed description is included to provide further information about the present patent application.

5

Figures 12, 13:
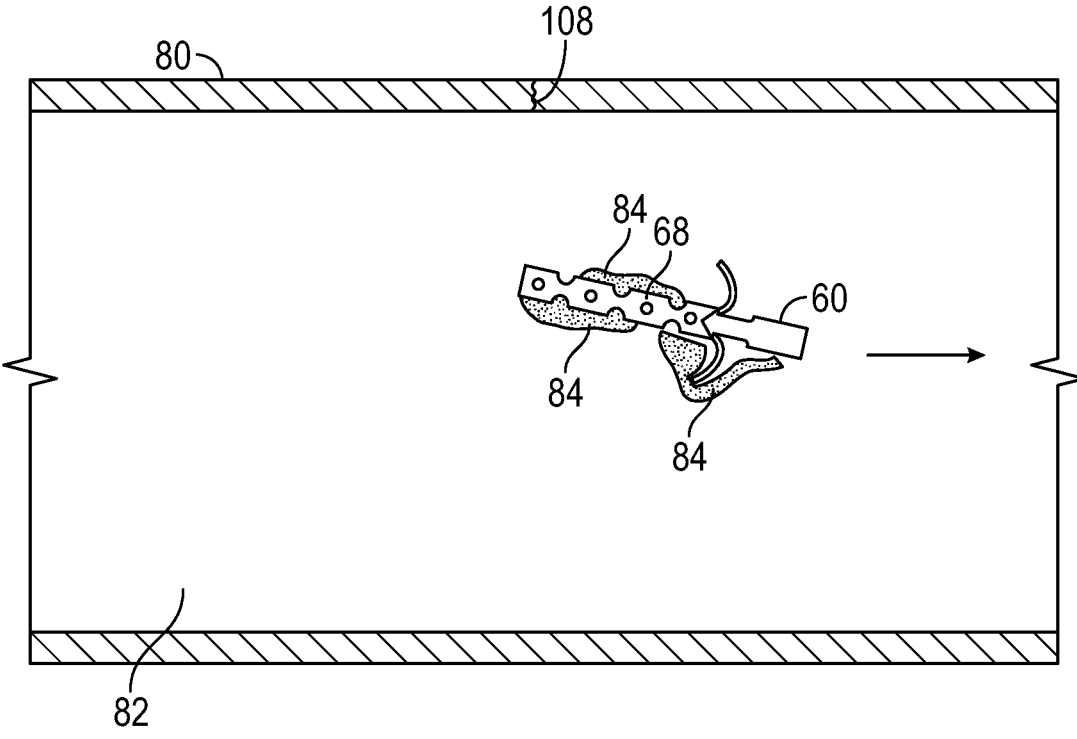
FIG. 12 illustrates a schematic representation of the inverted diverticulum and portion of the treatment device being expelled from the patient.
FIG. 13 illustrates a cross-sectional view of a treatment device, in accordance with one example of the present disclosure.
Figure 18:
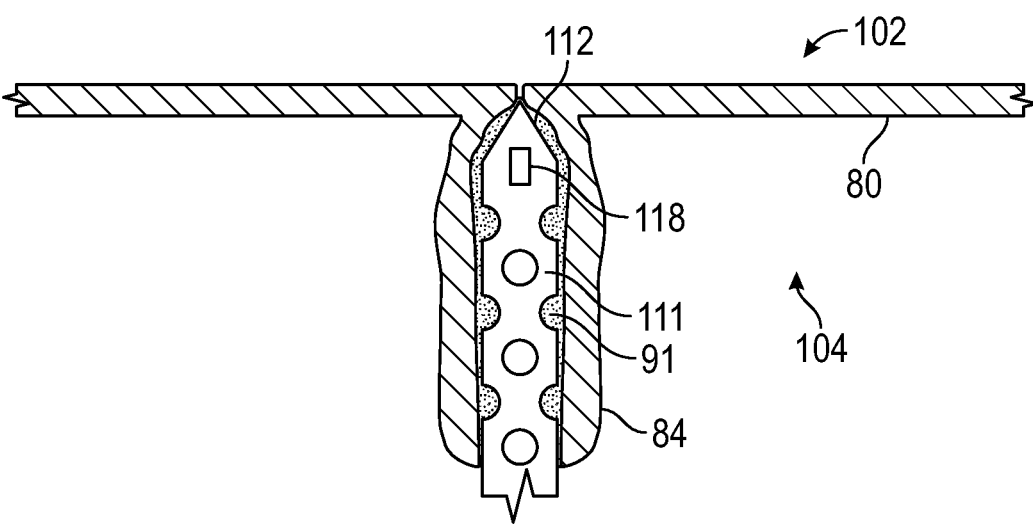

FIG. 18 illustrates a collapsed inverted diverticulum around a broken off treatment device in FIG. 13, in accordance with one example of the present disclosure.

Figure 19:
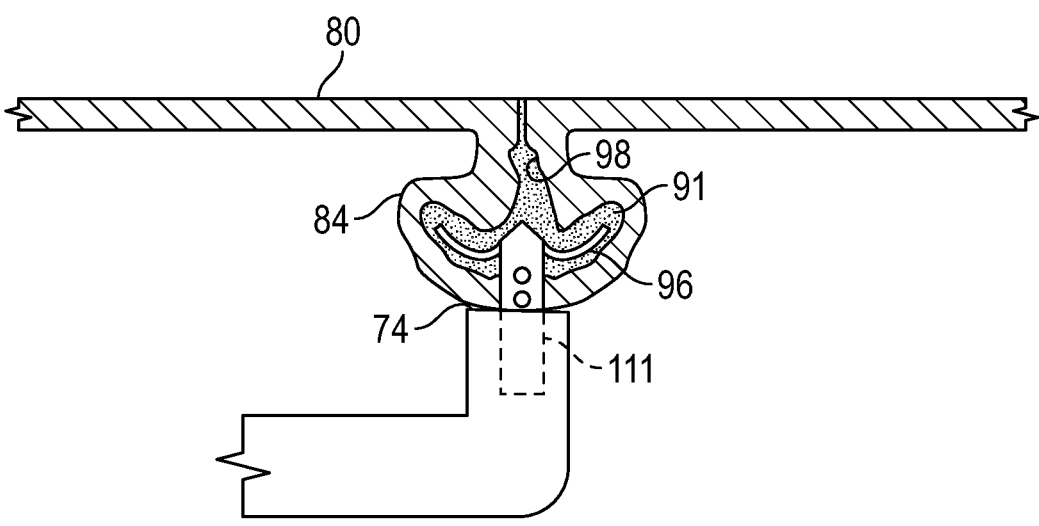

FIG. 19 illustrates a schematic representation of treating a diverticulum, in accordance with one example of the present disclosure.

Figure 20:
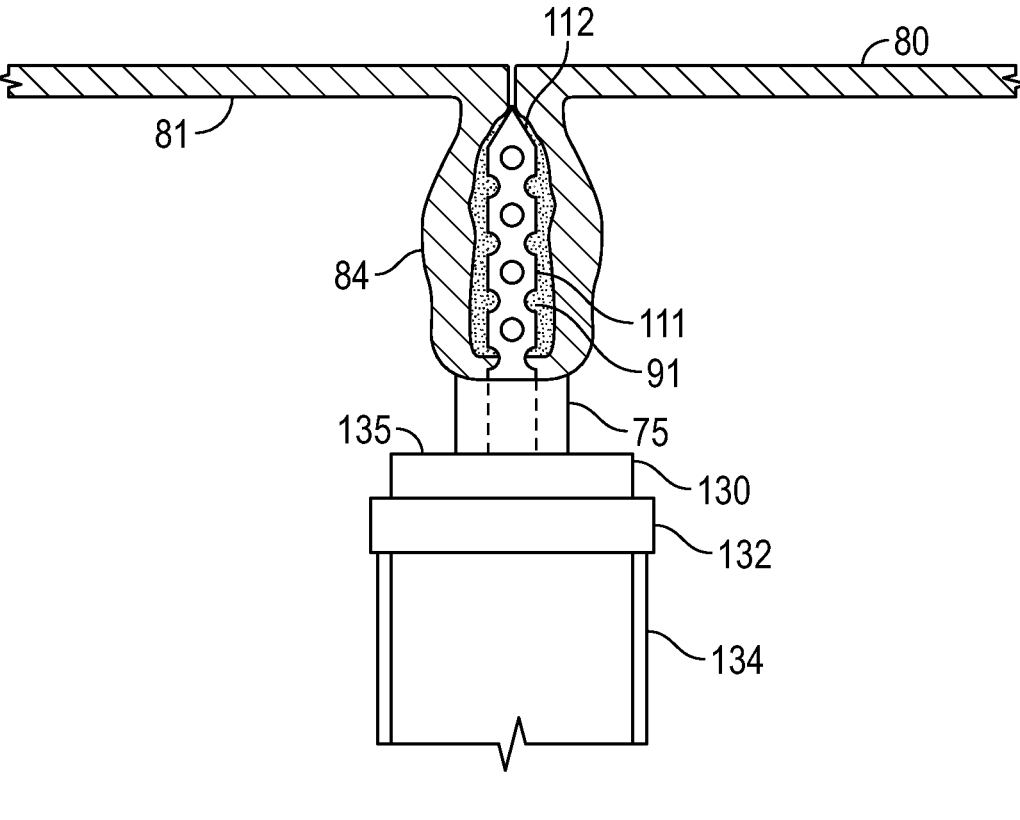

FIG. 20 illustrates a schematic representation of an elastic ring being delivered to an inverted and collapsed diverticulum, in accordance with one example of the present disclosure.

Figure 21:
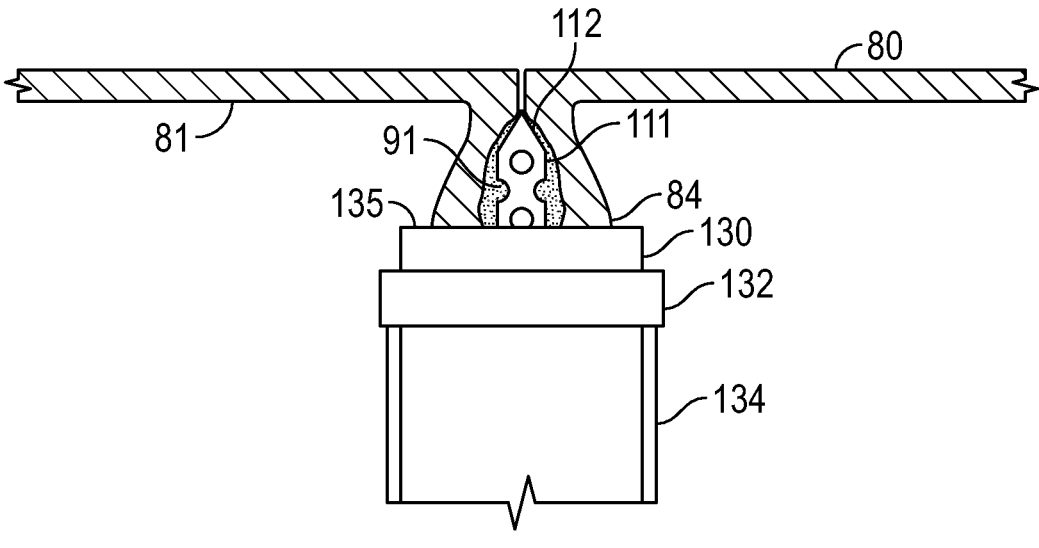

FIG. 21 illustrates a schematic representation of the elastic ring in FIG. 20 being advanced over the inverted and collapsed diverticulum, in accordance with one example of the present disclosure.

Figure 22:
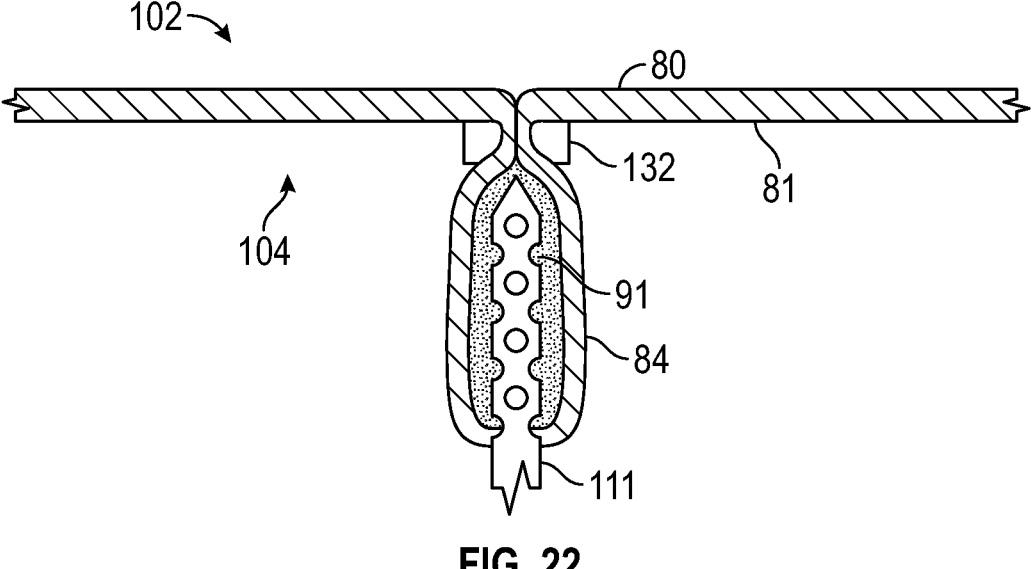

FIG. 22 illustrates a schematic representation of the elastic ring in FIGS. 20-21 positioned at a base of the inverted diverticulum, in accordance with one example of the present disclosure.

Figure 23:
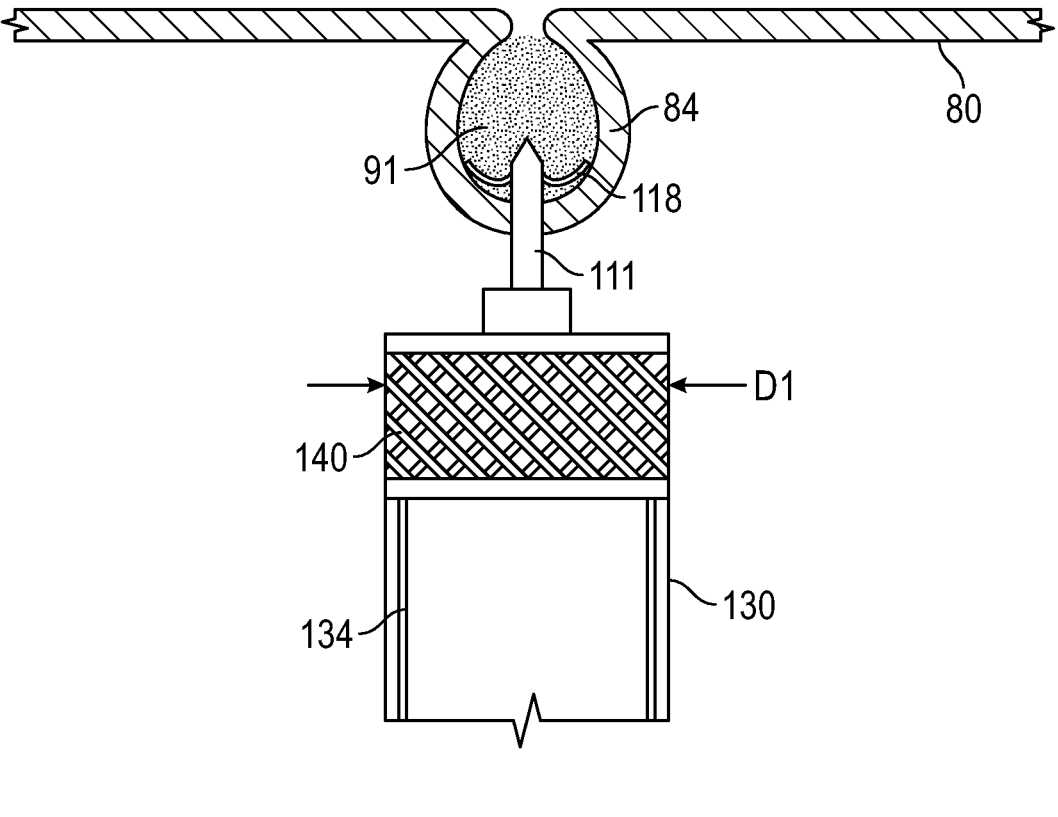

FIG. 23 illustrates a schematic representation of a collapsible stent, in accordance with one example of the present disclosure.

Figure 24:
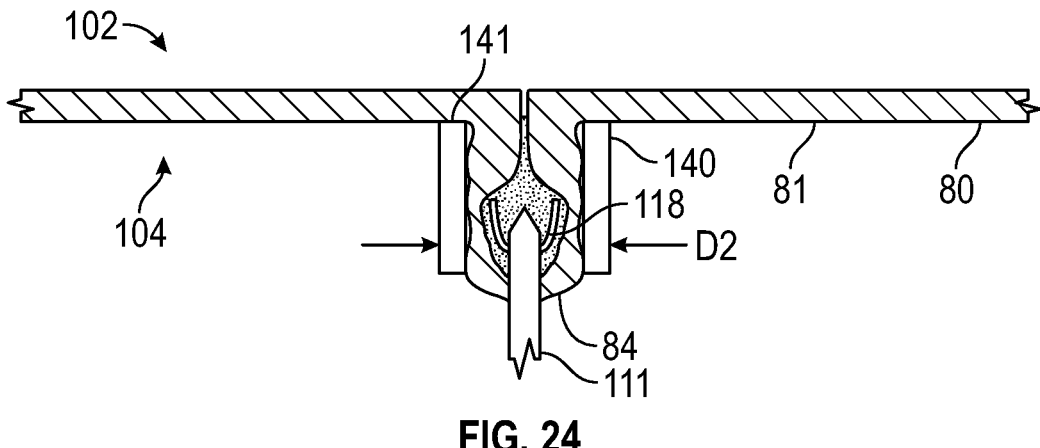

FIG. 24 illustrates a schematic representation of the collapsible stent in FIG. 23 positioned around the inverted diverticulum, in accordance with one example of the present disclosure.

Figure 25:
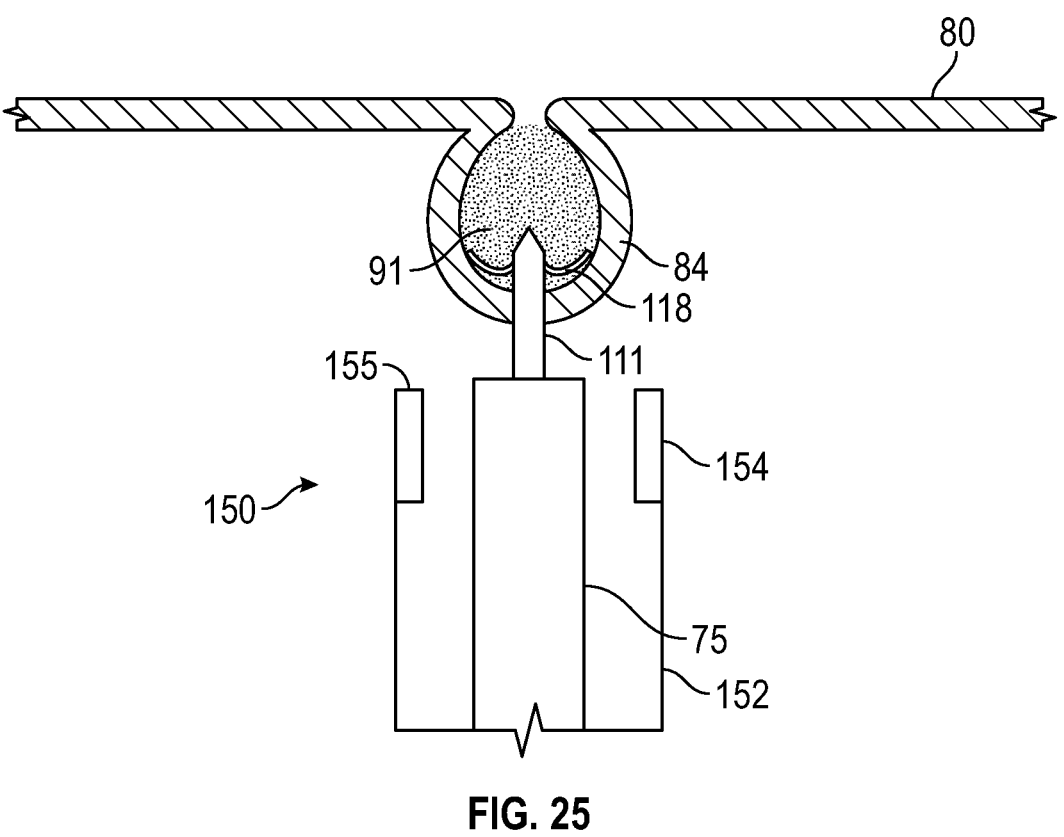

FIG. 25 illustrates a schematic representation of a collapsing device, in accordance with one example of the present disclosure.

Figure 26:
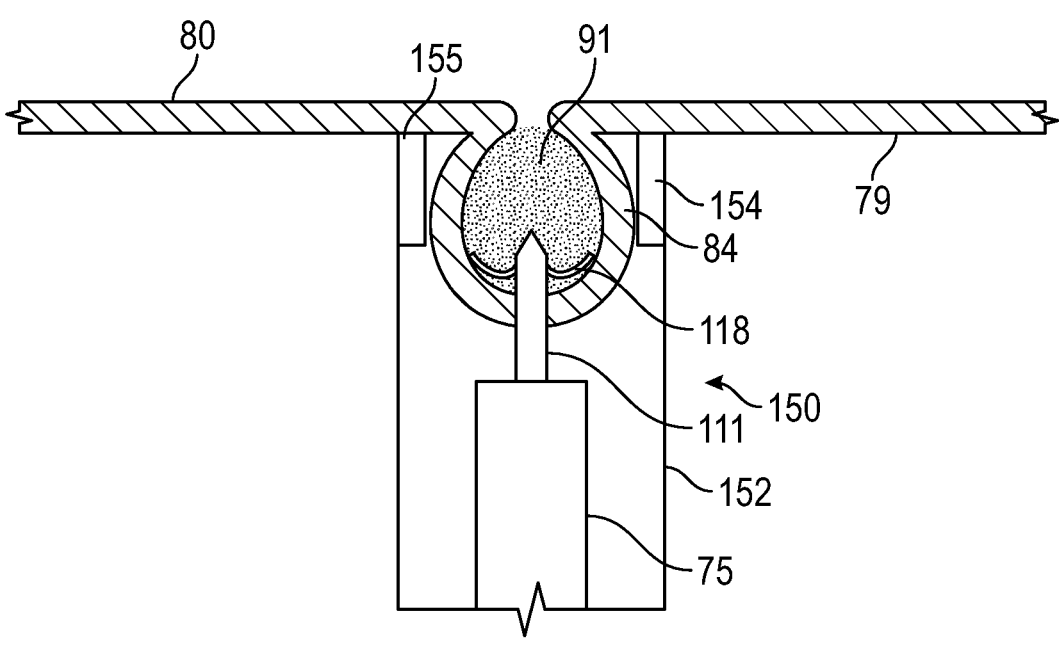

FIG. 26 illustrates a schematic representation of the collapsing device in FIG. 25 advanced over the inverted diverticulum, in accordance with one example of the present disclosure.

Figure 27:
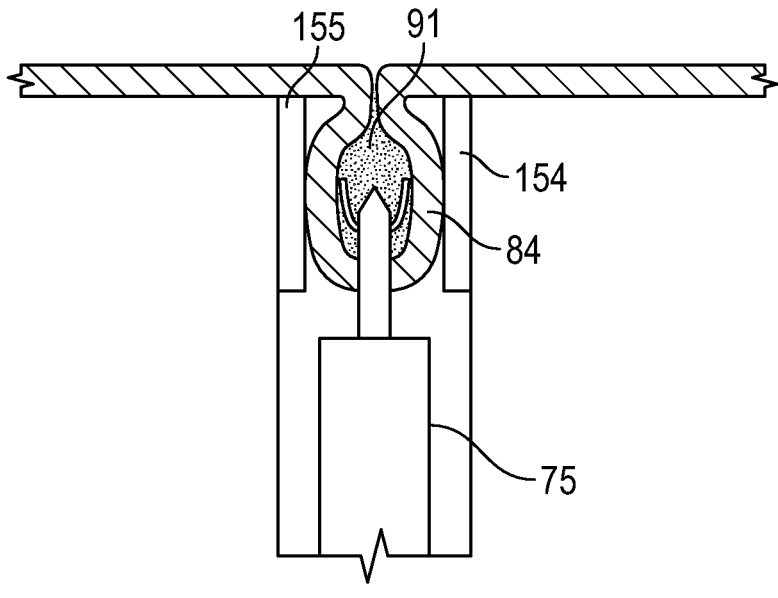

FIG. 27 illustrates a schematic representation of the collapsing device in FIG. 25 collapsing the inverted diverticulum, in accordance with one example of the present disclosure.

Figure 28:
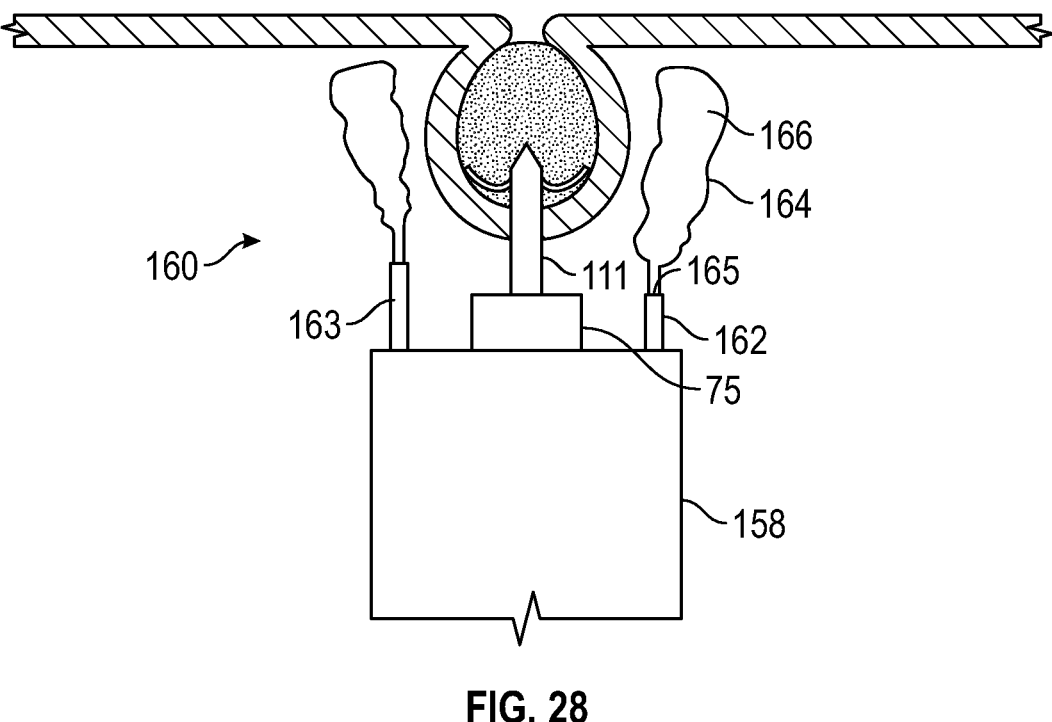

FIG. 28 illustrates a schematic representation of a collapsing device, in accordance with one example of the present disclosure.

Figure 29:
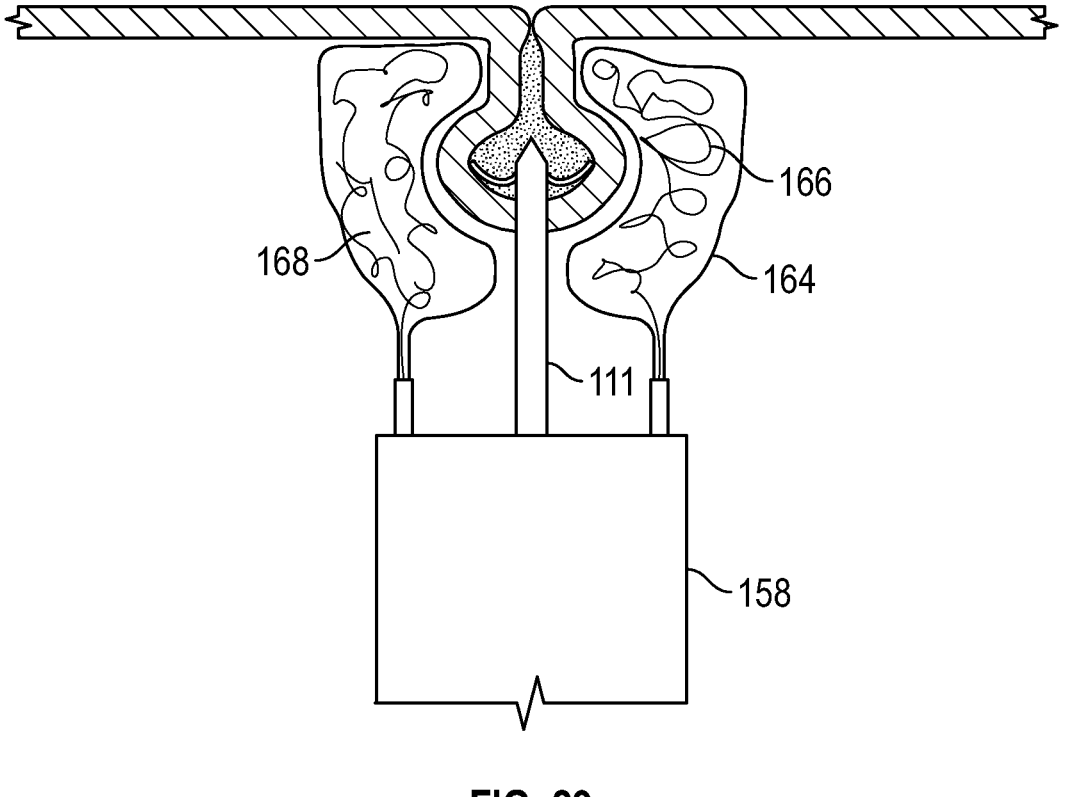

FIG. 29 illustrates a schematic representation of the collapsing device in FIG. 28 collapsing the inverted diverticulum, in accordance with one example of the present disclosure.

Figure 30:
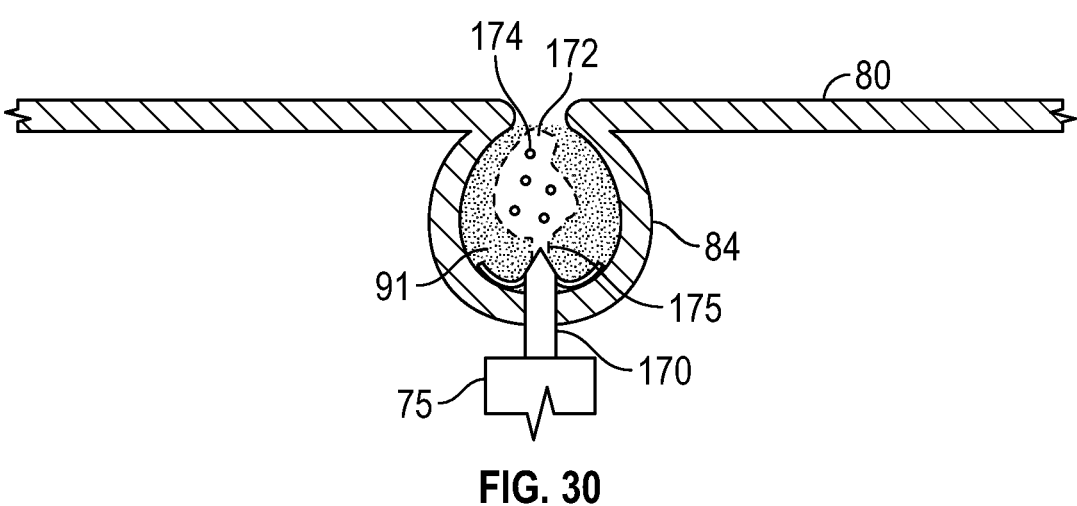

FIG. 30 illustrates a schematic representation of a collapsing device, in accordance with one example of the present disclosure.

FIG. 31 illustrates a schematic representation of the collapsing device in FIG. 30 contacting the inverted diverticulum, in accordance with one example of the present disclosure.

FIG. 32 illustrates a schematic representation of the collapsing device in FIG. 30 collapsing the inverted diverticulum, in accordance with one example of the present disclosure.

FIG. 33 illustrates a schematic representation of an inverted diverticulum including an elastic band and a portion of a treatment device, in accordance with one example of the present disclosure.

Figure 34:
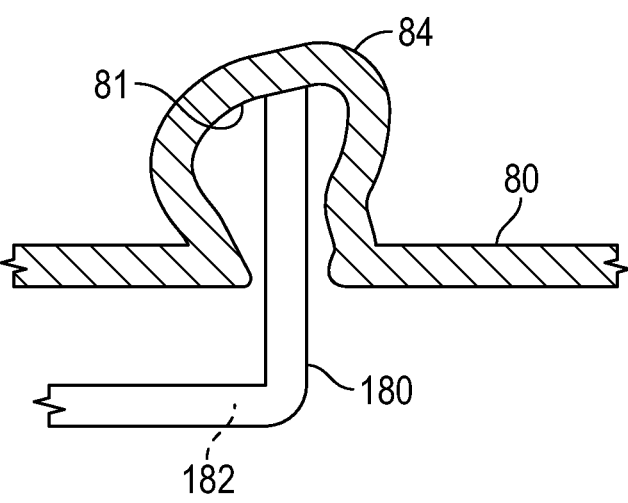

FIG. 34 illustrates a schematic representation of a treatment device to invert the diverticulum, in accordance with one example of the present disclosure.

Figure 35:
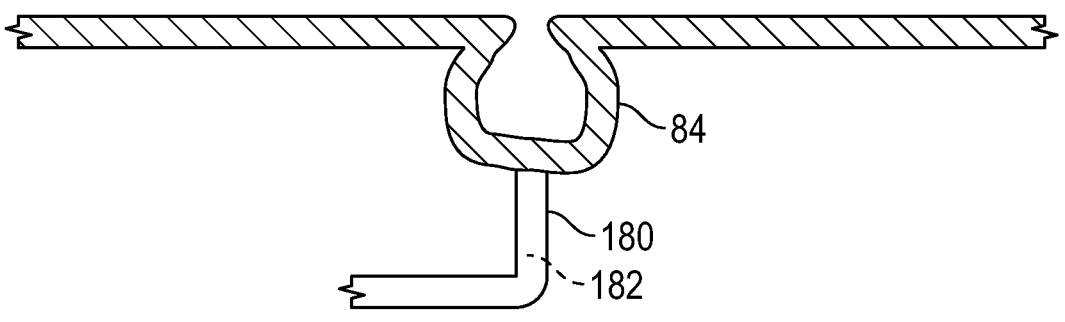

FIG. 35 illustrates a schematic representation of the treatment device of FIG. 34 after the diverticulum is inverted, in accordance with one example of the present disclosure.

6

Figure 36:
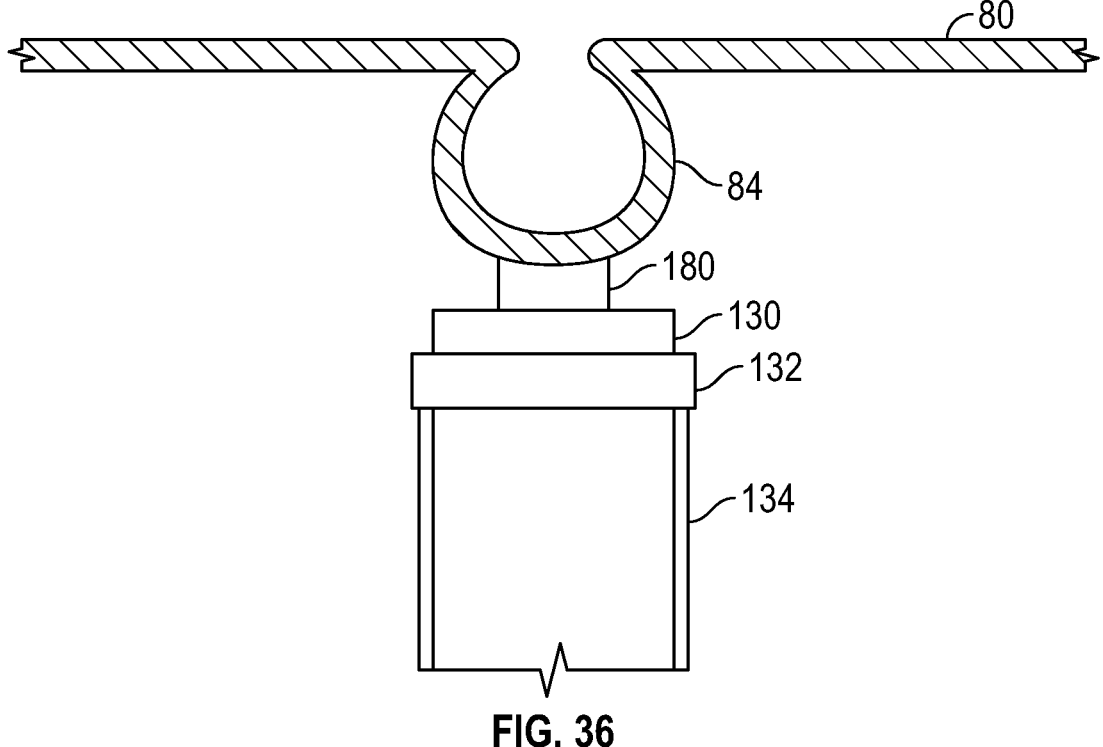

FIG. 36 illustrates a schematic representation of the treatment device in FIG. 34 and an elastic band, in accordance with one example of the present disclosure.

Figures 37, 38:
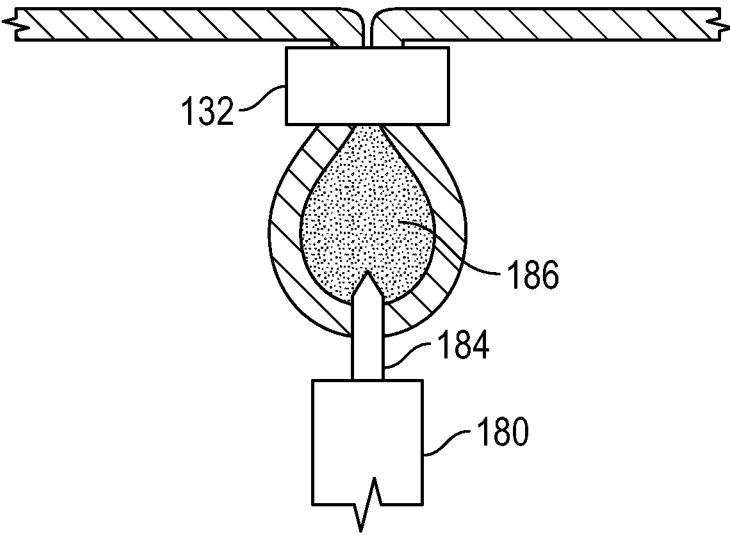

FIG. 37 illustrates a schematic representation of an inverted, banded, and filled diverticulum, in accordance with one example of the present disclosure.

FIG. 38 illustrates a schematic representation of another example of an inverted, banded, and filled diverticulum, in accordance with one example of the present disclosure.

Figures 39, 40:
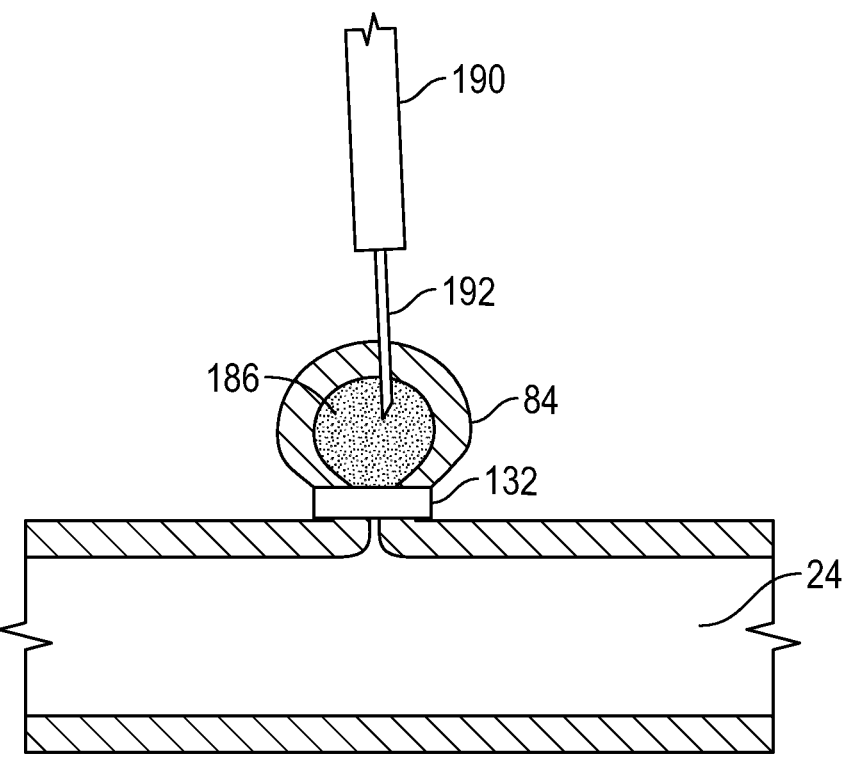

FIG. 39 illustrates a schematic representation of a banded and filled diverticulum, in accordance with one example of the present disclosure.

FIG. 40 illustrates a schematic representation of a banded and filled diverticulum, in accordance with one example of the present disclosure.

DETAILED DESCRIPTION

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Some embodiments described herein generally relate to devices, systems, and methods for treating diverticulitis, which is the inflammation or infected diverticula. As used herein, the term "diverticula" and "diverticulum" may refer to a sac- or pouch-like opening from a hollow organ or structure, such as the gastrointestinal (GI) tract, urinary tract, or respiratory tract. Although diverticula can occur in any tubular organ, diverticulosis is of greatest clinical relevance in the lower GI tract (large bowel or colon). Such diverticula may become inflamed or infected, may develop granulomas or may bleed.

Disclosed herein are tools, devices, assemblies, and methods for inverting and closing diverticula in a body lumen. The tools, devices, and assemblies may be configured for endoscopic delivery, e.g., through a working channel of a colonoscope. The tools, devices, and assemblies may alternatively be configured for laparoscopic delivery, e.g., to the outer surface of the colon.

Figure 1:
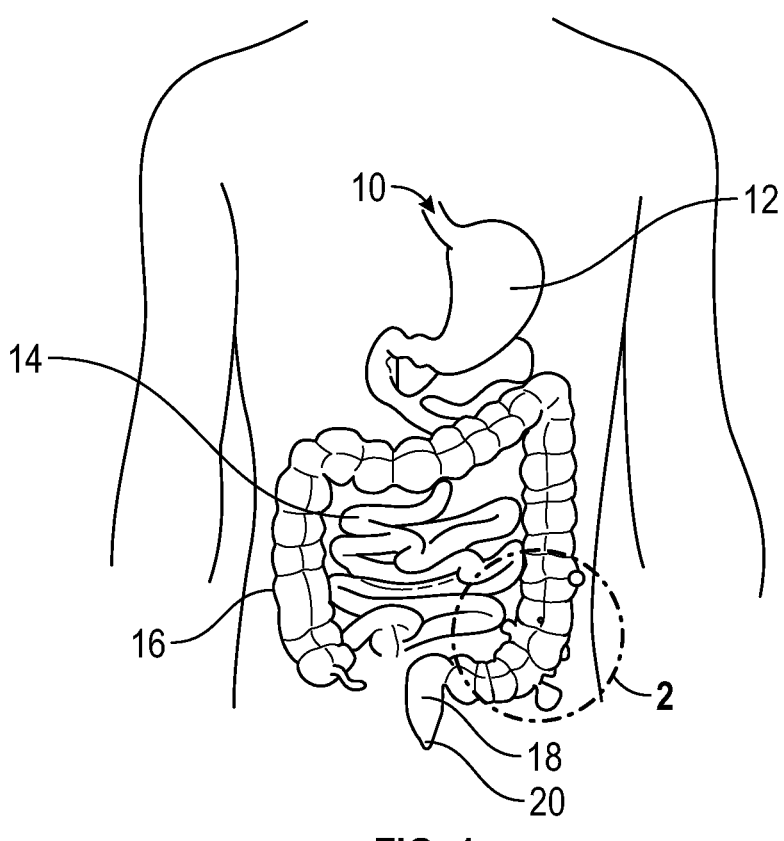
FIG. 1 illustrates a schematic representation of a human digestive tract.
Figure 2:
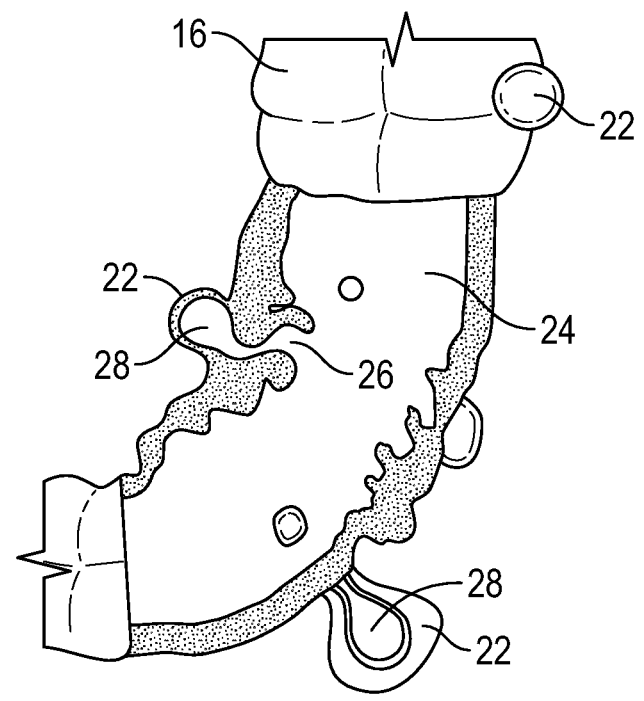
FIG. 2 illustrates a schematic representation of portion "A" in FIG. 1.

FIG. 1 illustrates a schematic representation of a human digestive tract. The digestive tract can be viewed as extending from the mouth, through the throat, down the esophagus 10 into the stomach 12 and to the small intestine 14, proceeding through the colon 16 (large intestine) to the rectum 18 and terminating at the anus 20. FIG. 2 illustrates a close-up view of section "A" in FIG. 1 and shows the presence of diverticula 22 in the colon 16. As seen in FIG. 2, the diverticula 22 are pouch-like structures or projections that extend from or through the walls of the digestive tract, such as at the colon 16. The diverticula 22 extend from a digestive tract lumen 24 (also referred to herein as "colon lumen 24") and define an ostia 26 (the opening) and a cavity 28.

Figures 3, 4:
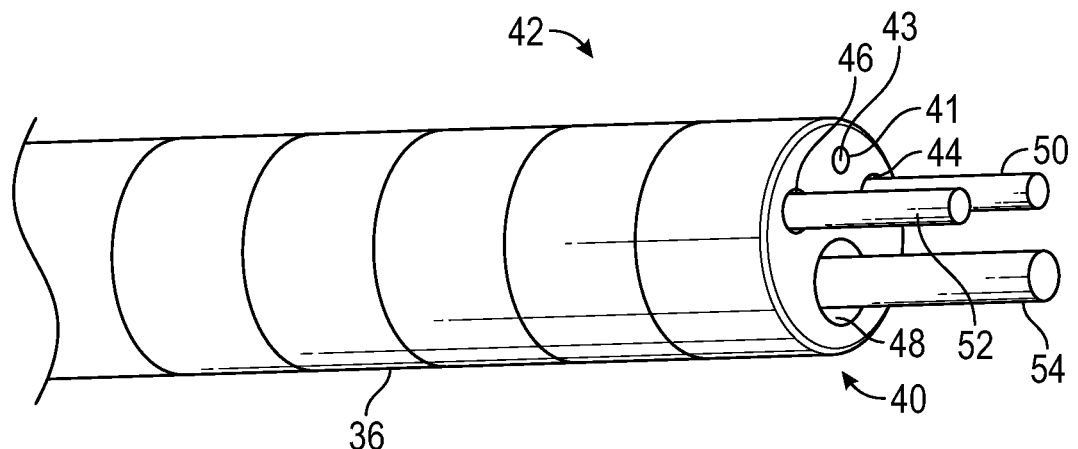
FIG. 3 illustrates a schematic representation of an endoscopic system for treating a diverticulum, in accordance with one example of the present disclosure.
FIG. 4 illustrates a perspective view of a working end of the endoscopic device of FIG. 3, in accordance with one example of the present disclosure.

FIG. 3 illustrates an endoscopy system 30 including an endoscopic device 32 (also referred to herein as "endoscope 32") and FIG. 4 illustrates a perspective view of a working portion 40 of the shaft 36. The system 30 of FIG. 3 is an illustrative example of an endoscopy system 30 suitable for use with the systems, devices and methods described herein, such as treatment and prevention of diverticulitis. The endoscopic device 32 can include a main body 34 (e.g., handle) and a shaft 36. The shaft 36 can extend from the main body 34 and have a working portion 40 at a distal end 42 of the shaft 36. The shaft 36 can be semi-rigid or semi-flexible such that manipulation of the shaft 36 within an anatomical structure (e.g., colon, sigmoid colon, descending colon, rectum, colonic lumen, etc.) may easily be facilitated. In on example, shaft 36 can be selectively steered and is configured to be inserted into the color or large intestine of a patient.

In one example, the shaft 36 can be insertable into an anatomical region for imaging and to provide passage of one or more treatment devices for treatment, or one or more therapeutic devices for treatment of a disease state associated with the anatomical region.

In on example, the endoscope 32 can display, on a monitor 38, an image captured by an optical imaging system 41 at the working portion 40 of the shaft 36. Various channels (collectively referred to, hereafter, as simply a "channel") can provide functions for endoscopic examination and treatment, such as air insufflation, irrigation, and treatment tool insertion. The various channels are formed in the shaft 36 along the axial direction thereof. As shown in FIG. 4, the working portion 40 includes a plurality of channels 44, 46, 48 disposed coaxially through the shaft 36 to facilitate proximal and/or distal movement of any number of devices 50, 52, 54 therethrough. In this manner, devices 50, 52, 54 may be moved distally through shaft 36 to extend distally from working portion 40 such that devices 50, 52, 54 may be utilized to treat a desired surgical site (e.g., diverticula 22), as discussed in further detail herein. At least one channel is a device channel, e.g., channel 48, is in communication with an instrument port 56 of the endoscope 32.

In one example, the optically imaging system 41 can also be incorporated into the shaft 36 such that the user can visualize the surgical site. The optically imaging system 41 can include, for example, but not limited to, a camera 43 and a light source 35.

In one example, the device 50 may be a suction device and/or an aspirator configured to remove undesirable materials from diverticula for purposes of treating diverticulitis. For example, device 50 may be used to remove, via suction and/or aspiration, feces and other materials from a diverticulum. With this purpose in mind, device 50 may be operably connected to a suitable suction source or suction pump 37 to facilitate suction of material.

In one example, device 52 may be an irrigation or lavage device configured to flush out the cavity of an organ or wound utilizing fluid (e.g., water or an antiseptic agent) expelled from the device 52. More specifically, the device 52 may be operably connected to a suitable fluid pump 39 to facilitate the expulsion of fluid from the device 52 for purposes of flushing out undesirable material from a diverticulum.

In one example, the system 30 can include a treatment device that is configured to treat and/or prevent diverticulitis by removing the diverticulum. As discussed herein, the diverticulum can be removed by treating the diverticulum bioactivity of the diverticulum is affected such that the diverticulum will eventually necrose and slough off. In one example, the device 54 is the treatment device configured to deliver treatment materials and/or devices to the diverticulum. The treatment device 54 can be inserted into the endoscope 32 through instrument port 56. The treatment device 54 can be coupled to a variety of devices 55 (activators, pumps, suction, etc.) that can be used with the treatment device 54 to treat the diverticulum.

Prior to treating the diverticulum with the device 54, devices 50, 52 can be used to remove any undesirable material (e.g., feces, pus, bacteria, blood, and/or other infected material) contained within a cavity of the diverticulum. For example, the working end 40 of the shaft 36 can be positioned proximate to the diverticulum. One appropriately placed, device 50 can be advanced from channel 44 and entered into a colon lumen (e.g., sigmoid colon, descending colon, rectum, etc.) and placed relative to a diverticulum such that the device 50 is proximate to the diverticulum. Once appropriately placed, device 50 can be utilized to, e.g., aspirate or suction the diverticulum 50. For example, device 50 can be activated such that aspiration and/or suction generated by a suction pump 37 connected to the device 50 can remove the unwanted material contained within the cavity of the diverticulum.

Subsequent to, prior to, or substantially simultaneously to aspirating a diverticulum, the device 52 may be utilized to lavage or irrigate the diverticulum. In one example, device 52 is a lavage device and can be advanced from the distal end 42 and is placed proximate to the diverticulum. The device 52 can then be utilized to "wash out" or flush the diverticulum of any undesirable materials (e.g., feces, blood, etc.) using the pressurized expulsion of fluid (e.g., water, saline, etc.) generated by a suitable fluid pump 39 operably connected to the device 52. In some scenarios, the step of flushing a diverticulum may not be necessary, for example, depending on the result of the aspiration step. Like-wise, in some scenarios, flushing a diverticulum may be performed prior to the step of aspirating the diverticulum and, depending on the result thereof, may render the aspirating step unnecessary.

Once the diverticula has been aspirated and/or flushed, the device 54 (also referred to herein as "treatment device") may be utilized to treat the diverticulum. In one example, the device 54 can be inserted through the instrument port 56 of the endoscope 32 for guidance through the channel 48 in the shaft 36 of the endoscope 32 to the diverticulum along the inner lining of the colon 16.

Figure 5:
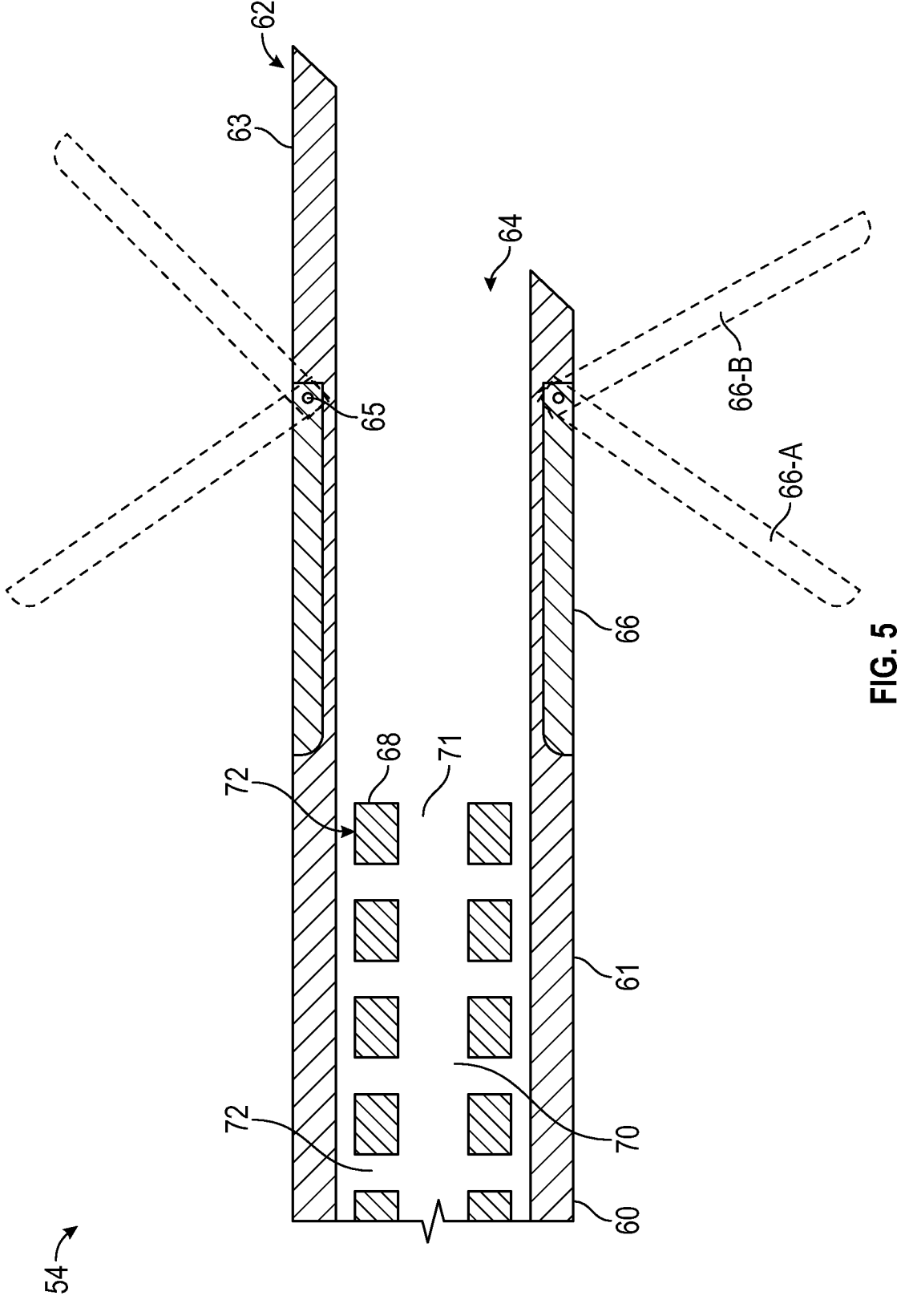
FIG. 5 illustrates a cross-sectional view of a treatment device, in accordance with one example of the present disclosure.

FIG. 5 illustrates a cross-sectional view of treatment device 54, according to one example of the present disclosure. The device 54 can include a needle 60 having a body 61 extending from a tip 63 at the distal end 62. As discussed herein, the tip 63 can be configured to pierce a wall of the diverticulum. In one example, the needle 60 can include one or more arms 66 (also referred to herein as "arms 66" and individually as "arm 66") that are configured to extend from the body 61. As seen in FIG. 5, the arms 66 can be configured to extend from an unexpanded position to one or more expanded positions 66-A and 66-B. In one example, the arms 66 can rotate about a pivot point 65. As discussed herein, once the wall of the diverticulum is pierced, the arms 66 are configured to expand and engage and invert the diverticulum. While shown as rotating about the pivot point 65, other mechanisms for having arms 66 expanding from the body 61 and engage the diverticulum are contemplated.

In one example, the needle 60 or portions of the needle 60 are formed from shape memory materials such as shape memory alloys. The use of a shape memory materials in medical devices is well known in the art and those skilled in the manufacture and use of medical devices having component(s) made from shape memory materials will appreciate its utility in the descriptions herein. In addition to shape memory materials, any component of any embodiment described herein may be made from any medical grade material, including but not exclusively limited to any metal, alloy, polymer, fiber, ceramic, or any combinations thereof.

In one example, the arms 66 can be spring loaded such that their natural unbiased state is in the expanded state. As the needle 60 pierces and passes through the wall of the diverticulum, the arms 66 can collapse. Once the arms 66 clear the wall of the diverticulum, the arms 66 can transition from the collapsed state to the uncollapsed state (e.g., expanded state).

In one example, the needle 60 can define a lumen 64. In one example, a conduit 68 can be configured to move within or be positioned within the lumen 64 of the needle 60. The conduit 68 defines a lumen 70. In one example, the conduit 68 is open-ended and has an opening 71 positioned at a distal end 72. In one example, the conduit 68 can be close ended. In one example, the conduit 68 can be perforated and includes a plurality of openings 72 located along the conduit 68. As discussed herein, the conduit 68 can be advanced from the needle 60 once the diverticulum is inverted.

FIGS. 6-12 illustrate systems, devices, and methods for treating a diverticulum. For purposes of discussion, the method illustrated by FIGS. 6-12 is shown to include the use of treatment device 54 in conjunction with the endoscope 32 described in FIGS. 3 and 4. However, the method illustrated by FIGS. 6-12 and described in detail below, may be employed utilizing any suitable endoscopic device in conjunction with any suitable surgical instruments for effecting the treatment of diverticulitis and/or the diverticulum detailed below.

Figure 6:
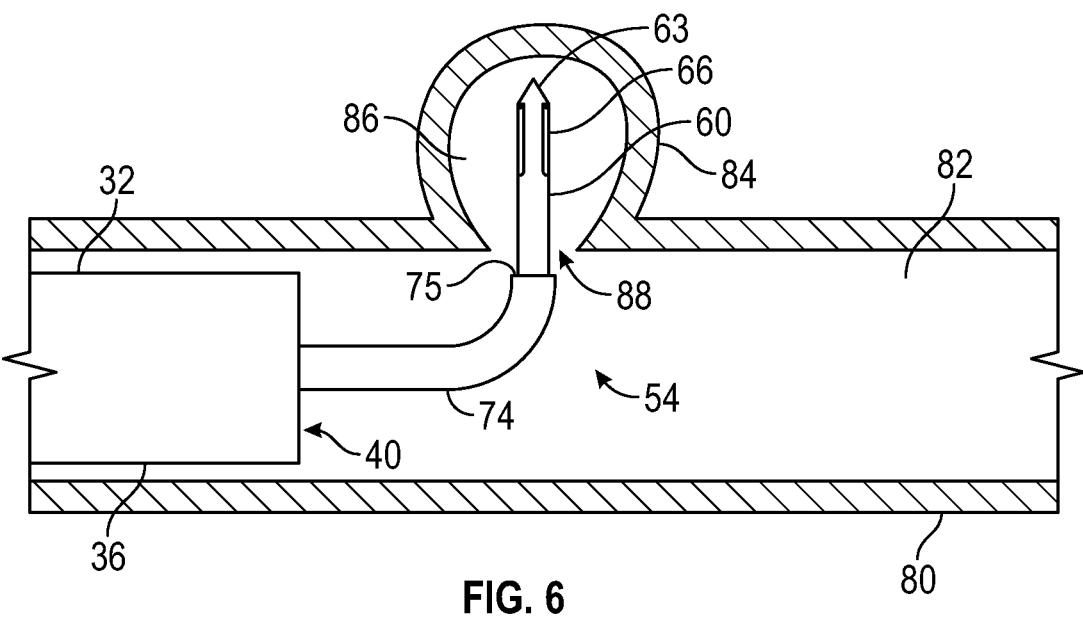
FIG. 6 illustrates a schematic representation of the treatment device in FIG. 5 in use to illustrate a method of treating a diverticulum, in accordance with one example of the present disclosure.

Referring to FIG. 6, the shaft 36 of the endoscope 32 is initially entered into a colon lumen 82 (e.g., sigmoid colon, descending colon, rectum, etc.) and placed relative to a target diverticulum (e.g., diverticulum 84) such that the working portion 40 is proximate to the diverticulum 84. In one example, the device 54 can include a delivery shaft 74 and the delivery shaft 74 can be advanced until a distal end 75 of the delivery shaft 74 is adjacent to the ostia 88 (i.e., opening) of the diverticulum 84. Once appropriately placed, the needle 60 can be advanced from, e.g., the delivery shaft 74, and extend through the ostia 88 and into a cavity 86 of the diverticulum 84.

Figure 7:
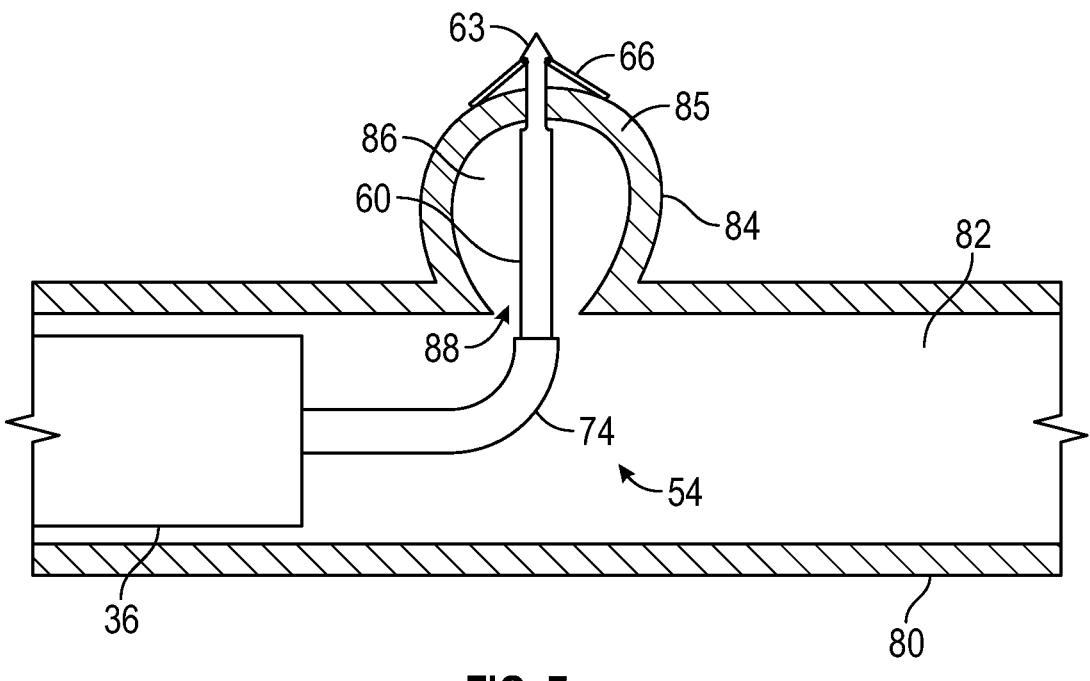
FIG. 7 illustrates a schematic representation of the treatment device in FIG. 5 in use to illustrate piercing the diverticulum, in accordance with one example of the present disclosure.
Figure 8:
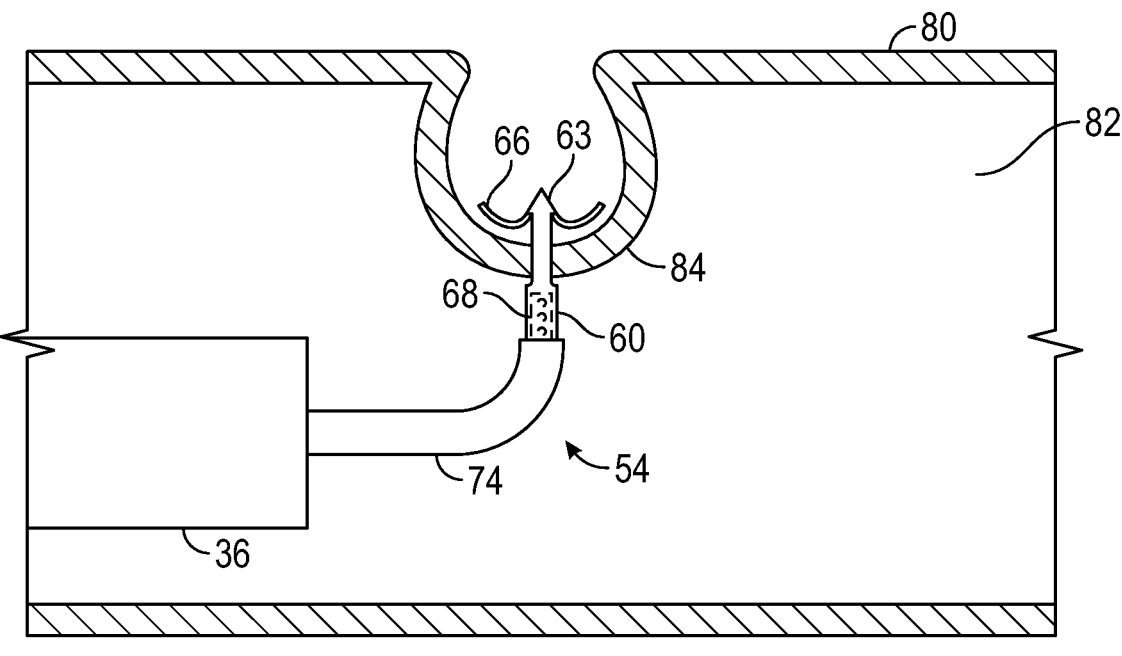
FIG. 8 illustrates a schematic representation of the treatment device in FIG. 5 in use to illustrate inverting the diverticulum, in accordance with one example of the present disclosure.
Figure 9:
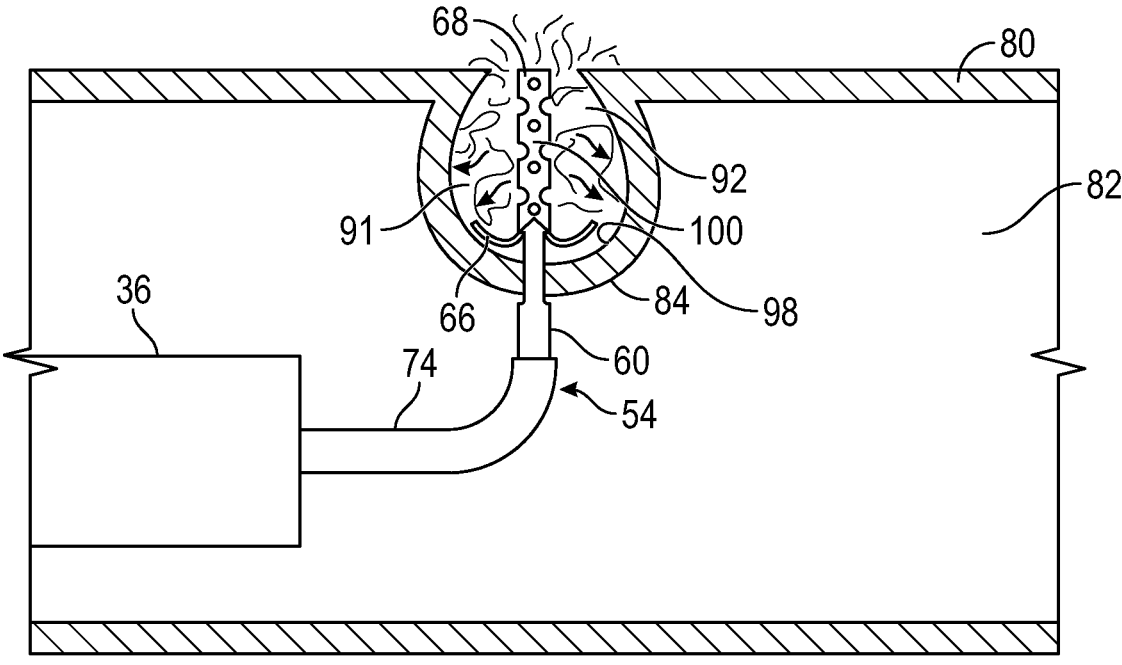
FIG. 9 illustrates a schematic representation of the treatment device in FIG. 5 in use to illustrate delivering a bioadhesive to the inverted diverticulum, in accordance with one example of the present disclosure.

Referring to FIG. 7, the needle 60 can be further advanced from the delivery shaft 74 such that it pierces a wall 85 of the diverticulum 84. The arms 66 can expand so that the diverticulum 84 is "captured" by the needle 60 and can be inverted. Referring to FIG. 8, the needle 60 can be retracted to invert the diverticulum 84. For example, the needle 60 can be pulled back into the delivery shaft 74 until the diverticulum 84 has been inverted. The arms 66 can be somewhat pliable such that they can flex, while still engaging the diverticulum 84. Referring to FIG. 9, the conduit 68 can be advanced from the needle 60 into a cavity 92 of the inverted diverticulum 84. Once in position, a bioadhesive can be delivered to the cavity 92 by the conduit 68. In one example, the bioadhesive can be selected from, but not limited to, tragacanth, Sodium alginate, Karaya gum, Guar gum, Xanthan gum, Soluble starch, Gelatin, Pectin, Chitosan, among others, etc. In general, any bioadhesive can be used that can promote mucoadhesion. Referring to FIG. 1, device 54 can be operationally coupled to device 55, e.g., which can be a pump to deliver the bioadhesive through the device 54.

In one example, the bioadhesive can be applied to generally the cavity 92 of the inverted diverticulum 84. In one example, the bioadhesive can optionally be applied such that a portion of the bioadhesive extends beyond the inverted diverticulum. For example, the bioadhesive can be applied such that a portion 101 (e.g., see portion 101 in FIGS. 10 and 11) of the bioadhesive is positioned on the external surface of the colon 80. That is, the cavity 92 of the inverted diverticulum 84 can be overfilled.

Figure 10:
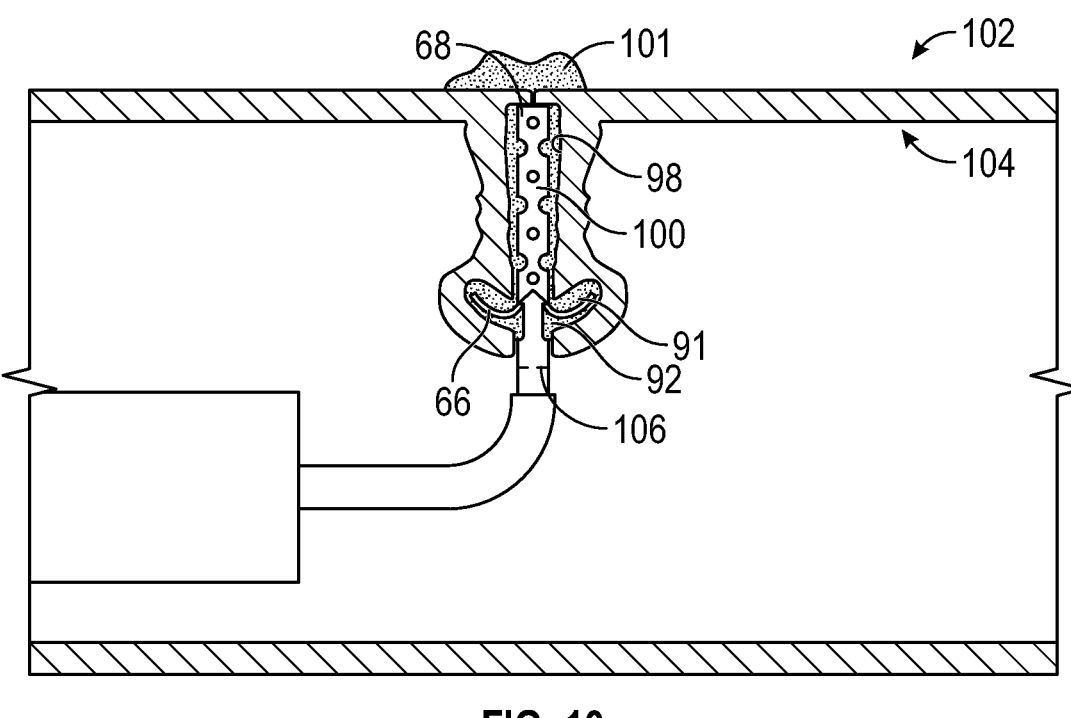
FIG. 10 illustrates a schematic representation of the treatment device in FIG. 5 in use to illustrate collapsing the inverted diverticulum around the treatment device, in accordance with one example of the present disclosure.

Once the bioadhesive 91 has been applied, suction can be applied to the lumen 70 of the conduit 68 to draw the diverticulum 84 towards the conduit 68. For example, device 55 (see FIG. 3) can be replaced such that device 55 is now a vacuum or a device that can apply suction to the cavity 92 of the inverted diverticulum 84. Referring to FIG. 10, after the vacuum/suction is applied, the inner surface 98 of the inverted diverticulum 84 can attach to portions of itself and/or portions of the conduit 68. For example, the inner surface 98 can attach to itself and/or an outer surface 100 of the conduit 68. As seen in FIG. 10, the cavity 92 of the inverted diverticulum 82 has been reduced and generally conforms to the shape of the conduit 68 and needle 60 that are positioned within the cavity 92.

As discussed herein, if the cavity 92 is overfilled and the portion 101 (e.g., a bulge) of the bioadhesive is on the external surface of the colon 80, after suction, the bulge of bioadhesive can still be present to assist in securing the opening of the inverted diverticulum 84.

Figure 11:
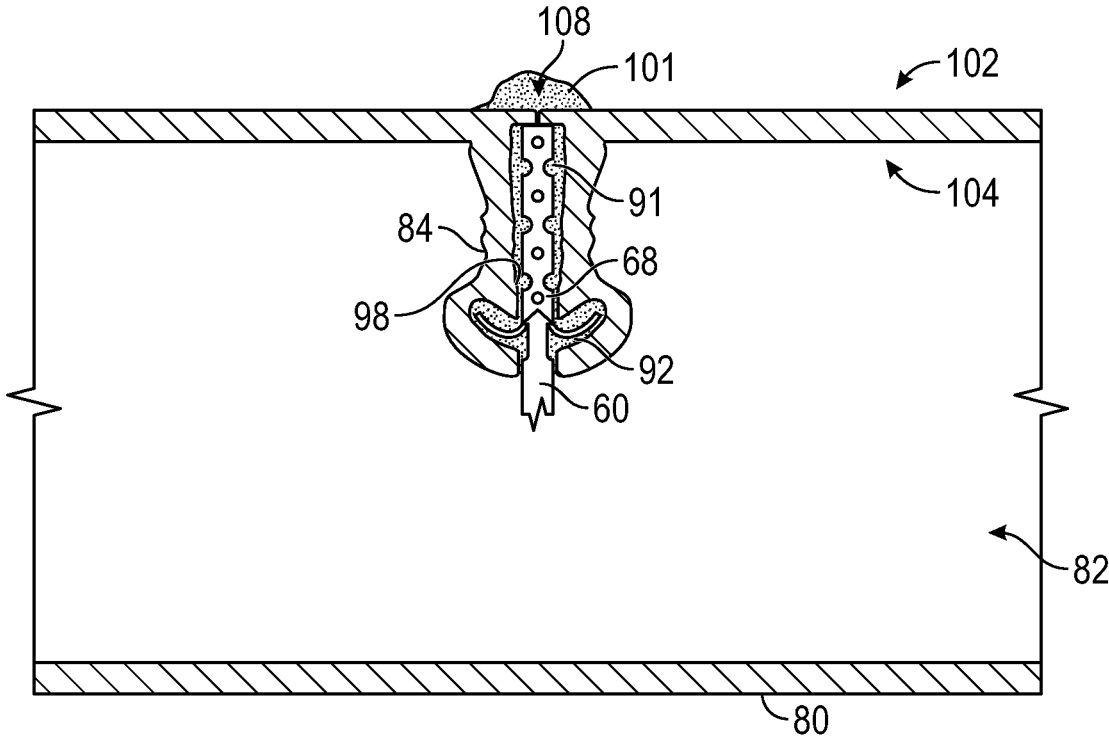
FIG. 11 illustrates a schematic representation of the treatment device in FIG. 5 in use to illustrate breaking off a portion of the treatment device, in accordance with one example of the present disclosure.

Referring to FIG. 11, once sufficient suction/vacuum and been applied, the needle 60 and the conduit 68 can be cut (or broken off) such that the portion of the needle 60 and the conduit 68 positioned within the inverted diverticulum 84 are released from the remaining portion of the treatment device. In one example, a separate cutting device can be used to cut through the needle 60 and the conduit 68. In one example, the needle 60 and/or the conduit 68 can include one or more predetermined breakaway lines (e.g., breakaway line 106) such that the portion of the needle 60 and the conduit 68 positioned in the inverted diverticulum 84 can break away from the remaining portions at the appropriate breakaway line. As seen in FIG. 11, the shaft 36, delivery shaft 74, and remaining portions of the needle 60 and the conduit 68 have been removed from the colon lumen 82

Adhering the inner surface 98 of the cavity 92 of the inverted diverticulum 84 to itself and the conduit 68 allows the inverted diverticulum 84 to maintain a closed state. By maintaining the closed state, the diverticulum 84 can heal on a serosa side 102 of the colon 80 and necrose on the mucosa side 104, eventually falling off. That is, the serosa side 102 can heal shut, while the circulation of blood into the tissue of the inverted diverticulum 84 can be reduced and cause necrosis of the diverticulum 84. The necrotized diverticulum 84 may slough off while the serosa 102 at the base 108 of the inverted diverticulum 84 is adhered to itself and will begin to heal shut. As seen in FIG. 12, after a time period, the base 108 of where the inverted diverticulum 84 was has healed shut and the inverted diverticulum 84 has necrosed. As seen in FIG. 12, the portion of the needle 60 and conduit 68 that was left in the inverted diverticulum 84, as well as any remaining necrosed tissue of the inverted diverticulum 84, has sloughed off and can be expelled from the patient via the colon lumen 82.

While the bioadhesive and suction were used to close the inverted diverticulum, other methods can be used in addition to or alternatively to the methods and devices illustrated in FIG. 6-12. In one example, portions of the conduit 68 and/or portions of the needle 60 can be configured to deliver electrosurgical energy to the inner surface 98 of the inverted diverticulum 84. For example, referring to FIG. 10, in addition to or alternatively to the bioadhesive, after the vacuum has been applied to collapse the inverted diverticulum 84 onto the conduit 68, electrosurgical energy can be applied such that the inner surface 98 sticks to the portions of the conduit 68 and/or the portions of the needle 60 that applied the electrosurgical energy. By applying electrosurgical energy can cause the tissue to char and stick to the portions of the needle 60 and conduit 68 thereby further increasing the adhesion. In one example, besides electrosurgical energy other types of energy can be applied to the inverted diverticulum to cause the tissue of the diverticulum to stick to the treatment device. For example, heat, resistance heating, vibration, and cold therapy (e.g., cryotherapy), among others, can be used to cause the diverticulum to stick to itself and/or to the treatment device.

FIG. 13 illustrates another exemplary device 110 (treatment device) for treating a diverticulum. In one example, device 110 can include include needle 111 instead of using needle 60 and conduit 68 shown in FIGS. 6-12. The device 110 can be the treatment device used in conjunction with the endoscope 32 described in FIGS. 3 and 4.

As seen in FIG. 13, needle 111 includes a body 113 extending from a tip 112 at the distal end 114. The tip 112 is configured to pierce a wall of the diverticulum. A portion of the body 113 includes openings 120. The needle 111 can define a lumen 116 that is configured to, e.g., deliver a bioadhesive and/or apply a vacuum to a diverticulum. As discussed above with needle 60, the lumen 116, in one example, can extend through the needle 111 and have an opening 109 at the distal end 114. In another example, the lumen 116 can be closed on one end, e.g., at the distal end 114. Similar to needle 60, needle 111 can include one or more arms 118 that are configured to expand once the arms 118 clear the diverticulum to capture (e.g., couple to) the diverticulum, as discussed herein.

In one example, device 110 can further include a blocking tube 122. In one example, the blocking tube 122 can be positioned within the lumen 116. In another example, the bocking tube 122 can be positioned around the body 113 of the needle 111. The blocking tube 122 is configured to be translatable relative to the needle 111 such that the blocking tube 122 can seal off one or more openings of the needle 111.

Figure 14:
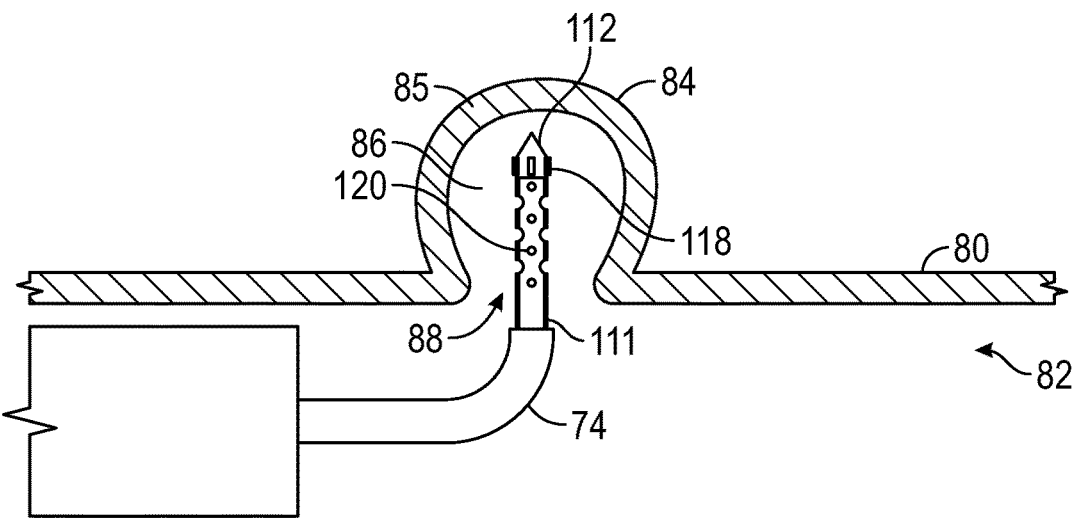
FIG. 14 illustrates a schematic representation of the treatment device in FIG. 13 in use to illustrate a method of treating a diverticulum, in accordance with one example of the present disclosure.
Figure 15:
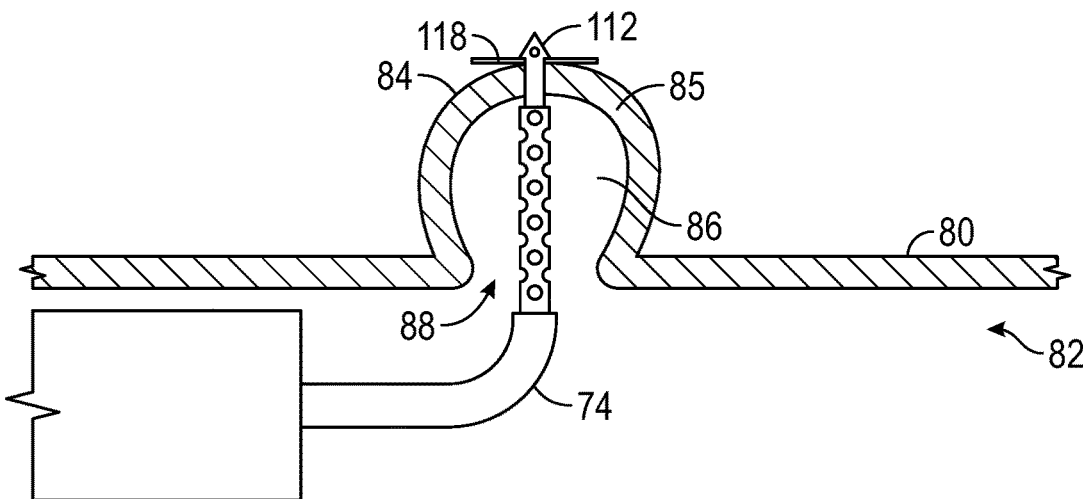
FIG. 15 illustrates a schematic representation of the treatment device in FIG. 13 in use to illustrate piercing the diverticulum, in accordance with one example of the present disclosure.
Figure 16:
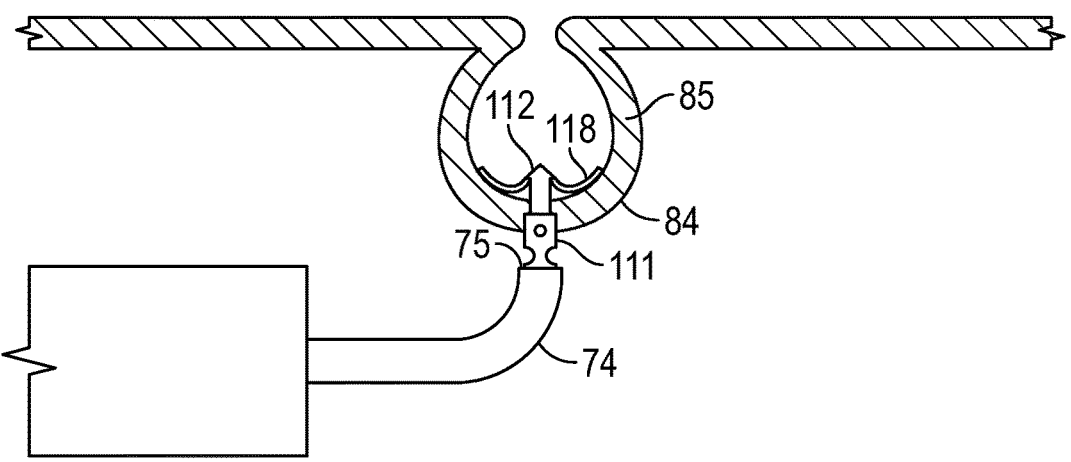
FIG. 16 illustrates a schematic representation of the treatment device in FIG. 13 in use to illustrate inverting the diverticulum, in accordance with one example of the present disclosure.
Figure 17:
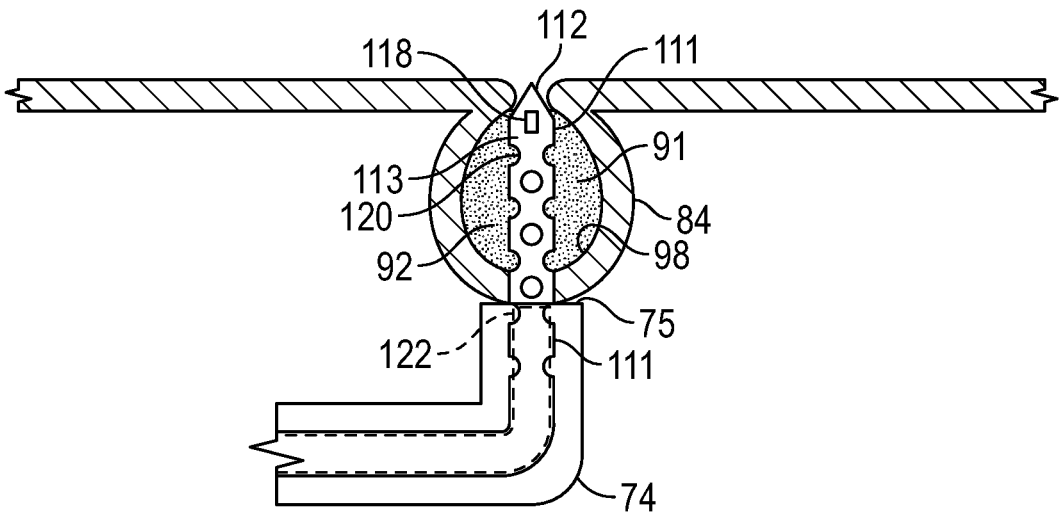
FIG. 17 illustrates a schematic representation of the treatment device in FIG. 13 in use to illustrate delivering a bioadhesive to the inverted diverticulum, in accordance with one example of the present disclosure.

FIGS. 14-18 illustrate an exemplary method for treating a diverticulum using device 110. In FIG. 14, the delivery shaft 75 can be advanced to be proximate to the ostia 88 of the diverticulum 84. The needle 111 can be advanced from the delivery shaft 75 until the needle 110 extends through the ostia 88 and into the cavity 86 of the diverticulum, as seen in FIG. 14. The needle 111 can continue to be advanced until the tip 112 pierces the wall 85 of the diverticulum, as seen in FIG. 15. Once the arms 118 extend past the wall 85 of the diverticulum 84 they can expand. In FIG. 16, the needle 111 can be retracted into the delivery shaft 74 until the diverticulum 84 is inverted. As seen in FIG. 16, the arms 118 can be somewhat pliable such that the arms 118 can extend beyond their initial expanded state, while still engaging with the diverticulum 84.

After the diverticulum 84 is inverted, the needle 111 can be again advanced, relative to the inverted diverticulum 84, to position the body 113 of the needle 111 within the cavity 92 of the diverticulum 84. In one example, the needle 111 can be advanced the same way as the needle was initially advanced into the diverticulum 84. That is, the needle 111 is advanced from the delivery shaft 75. However, in some examples, a vacuum can be applied through the delivery shaft 74. For example, the delivery shaft 74 can be advanced until the distal end 75 of the delivery shaft 74 abuts the inverted diverticulum 84 (see FIG. 17). A vacuum/suction can be applied to secure the position of the inverted diverticulum 84 while the needle 111 is advanced into the inverted diverticulum 84. In one example, the blocking tube 122 can be advanced to seal off the openings 122 of the needle 111 while the suction is being applied to the delivery shaft 74 such that the suction force is not in fluid communication with the lumen 116 of the needle 111.

Once the needle 111 had been advanced and is positioned within the inverted diverticulum 84, the bioadhesive 91 can be delivered. For example, the bioadhesive 91 can be delivered to the cavity 92 of the inverted diverticulum 84 through the lumen 116 (see FIG. 13) of the needle 111 and through the openings 120 and, optionally, out through the distal opening 109 (see FIG. 13) at the distal end 114. For example, the needle 111 can be operationally coupled to device 55 (see FIG. 3), e.g., which can be a pump to deliver the bioadhesive 91 through the needle 111. The blocking tube 122 can be used to block the bioadhesive 91 from exiting openings 120 that are not positioned within the inverted diverticulum 84. While not shown in FIG. 17, the bioadhesive 91 can be applied such that a bulge of bioadhesive 91 forms on the external surface of the colon 80, as discussed herein with respect to FIGS. 9-11.

Once the bioadhesive 91 has been applied, suction can be applied to the lumen 116 of the needle 111 to draw the diverticulum 84 towards the needle 111. For example, device 55 can be replaced such that device 55 is now a vacuum or device that can apply suction to the cavity 92 of the inverted diverticulum 84. Referring to FIG. 18, after the vacuum/suction is applied, the inner surface 98 of the inverted diverticulum 84 can attach to portions of itself and/or portions of the needle 111. For example, the inner surface 98 can attach to itself and/or an outer surface of the needle 111. As seen in FIG. 18, the cavity 92 of the inverted diverticulum 82 has been reduced and generally conforms to the shape of the needle 111 that is positioned within the cavity 92 of the inverted diverticulum 84.

Referring to FIG. 18, once sufficient suction/vacuum and been applied, the needle 111 is cut such that the portion of the needle 111 positioned within the inverted diverticulum 84 is released. In one example, a separate cutting device can be used to cut through the needle 111. In one example, the needle 111 can include predetermined breakaway lines such that the portion of the needle 111 positioned within the inverted diverticulum 84 can break away from remaining portions.

As discussed herein, adhering the inner surface 98 of the cavity 92 of the inverted diverticulum 84 to itself and the needle 111 allows the inverted diverticulum 84 to maintain a closed state. By maintaining the closed state, the diverticulum 84 can heal on a serosa side 102 of the colon 80 and necrose on the mucosa side 104, eventually falling off, as discussed herein.

In one example, portions of the needle 111 can be configured to deliver electrosurgical energy to the inner surface 98 of the inverted diverticulum 84. For example, referring to FIGS. 17 and 18, prior to breaking the needle 111, in addition to or alternatively to the bioadhesive, and after the vacuum has been applied to collapse the inverted diverticulum 84 onto the needle 111, electrosurgical energy can be applied such that the inner surface 98 sticks to the portions of the needle 111. By applying electrosurgical energy can cause the tissue to char and stick to the portions of the needle 111 thereby further increasing the adhesion. In one example, besides electrosurgical energy other types of energy can be applied to the inverted diverticulum to cause the tissue of the diverticulum to stick to the treatment device. For example, heat, resistance heating, vibration, and cold therapy (e.g., cryotherapy), among others, can be used to cause the diverticulum to stick to itself and/or to the treatment device.

In one example, instead of readvancing the needle 111 from the position in FIG. 16, once in the retracted state, the bioadhesive can be delivered and suction can be applied without advancing the needle 111, which is shown in FIG. 19. For example, suction can be applied through lumen 116 of needle 111 so that the inverted diverticulum 84 can collapse and adhere to itself and to a portion of the needle 111, as discussed herein. Optionally, suction can also be applied through the delivery shaft 74.

In the previous examples suction and/or bioadhesive has been disclosed as means for collapsing the inverted diverticulum. However, additional or alternative methods and devices can be combined or used separately to securely collapse the diverticulum such that the inverted diverticulum necroses, while the opening of the inverted diverticulum heals.

FIGS. 20-22 illustrate a step in treating the diverticulum. While FIGS. 20-22 are shown using needle 111, the methods and devices shown in FIGS. 20-22 can be used with any of the methods and devices disclosed herein. As shown in FIG. 20, the bioadhesive 91 has been delivered and suction has been applied so that the inverted diverticulum 84 has collapsed and has adhered to itself and/or the needle 111. Prior to breaking off the needle 111, a delivery sheath 130 can be advanced over the delivery shaft 75 to deliver a banding device, e.g., an elastic band 132 (referred to herein as "band 132"). The delivery sheath 130 can further include pushers 134 that are configured to move the band 132 from the delivery sheath 130 and deliver the band 132 around the inverted diverticulum 84. As seen in FIG. 21, the delivery sheath 130 has been advanced partially around the inverted diverticulum 84. Once the delivery sheath 130 has advanced such that a distal end 135 of the delivery sheath 130 contacts the inner surface 81 of the diverticulum 84, the pushers 134 can advance relative to the delivery sheath 130. The pushers 134 can advance to move the band 132 from the delivery sheath 130 to around the inverted diverticulum 84, as shown in FIG. 22.

Providing the band 132 can tighten the seal around the inverted diverticulum 84 to assist in maintaining the inverted diverticulum 84 in the closed state. As discussed herein, by closing the inverted diverticulum 84 allows the diverticulum 84 to heal on the serosa side 102 and necrose on the mucosa 104 side, eventually the tissue being absorbed or falling off, while the needle 111 and band 132 can fall off and be expelled from the patient.

The band 130 can be formed from, but limited to, a shape memory material or an elastic material. In on example, the band 130 can include a drug coating. The drug coating can include, but is not limited to, a coagulation modifier and an antibiotic to assist in the healing on the serosa side 102 and prevent infection, among others.

FIGS. 23 and 24 illustrate a step in treating the diverticulum. While FIGS. 23 and 24 are shown using needle 111, the methods and devices shown in FIGS. 23 and 24 can be used with any of the methods and devices disclosed herein. As shown in FIG. 23, the diverticulum 84 has been inverted and the bioadhesive 91 has been delivered. For simplicity, the openings and blocking tube (if used) of needle 111 are not shown. However, a needle similar to needle 111 without the openings along the side or the blocking tube can be used.

Prior to breaking off the needle 111, a delivery sheath 130 can be advanced over the delivery shaft 75 to deliver a collapsing device, e.g., a flexible stent 140 (referred to herein as "stent 140"). The delivery sheath 130 can further include the pushers 134 that are configured to remove the stent 140 from the delivery sheath 130 and deliver the stent 140 around the inverted diverticulum 84. As seen in FIG. 24, stent 140 has been positioned around the inverted diverticulum 84 such that a distal end 142 of the stent 140 is adjacent to the inner surface 81 of the colon 80. The stent 140 in FIG. 23 is in an expanded position. Once removed from the delivery sheath 130, the stent 140 collapses around the inverted diverticulum 84. For example, the stent 140 can have a first diameter "D1" and once removed from the delivery sheath 130, the stent 140 can collapse to a second diameter "D2". As the stent 140 collapses, the inverted diverticulum 84 also collapses. By collapsing around the inverted diverticulum 84, the surfaces of the inverted diverticulum 84 contact and adhere to itself and a portion of the needle 111. Depending on the collapsing force of the stent 140, the arms 118 of the needle 111 can be deformed, as shown in FIG. 24. In one example, suction applied via the needle 111 can be used in conjunction with the stent 140 to collapse and close the inverted diverticulum 84.

Providing the stent 140 can provide a compression force around the diverticulum and tighten the seal around the inverted diverticulum 84, which assists in maintaining the inverted diverticulum 84 in the closed state. As discussed herein, by closing the inverted diverticulum 84 allows the diverticulum 84 to heal on the serosa side 102 and necrose on the mucosa 104 side, eventually the tissue being absorbed or falling off, while the needle 111 and stent 140 can fall off and be expelled from the patient.

The stent 140 can be formed from, but not limited to, a shape memory material or an elastic material. In on example, the stent 140 can include a drug coating. The drug coating can include, but is not limited to, at least one of a coagulation modifier and an antibiotic to assist in the healing on the serosa side 102 and prevent infection.

The band 132 and the stent 140 in FIGS. 20-24 are illustrated as collapsing the inverted diverticulum 84 that includes the bioadhesive. However, in one example, the band 132 and the stent 140 can be used with or without the bioadhesive 92 being inserted into the inverted diverticulum 84.

FIGS. 25-27 illustrate an additional step to treating the diverticulum. While FIGS. 25-27 are shown using needle 111, the methods and devices shown in FIGS. 25-27 can be used with any of the methods and devices disclosed herein. As shown in FIG. 25, the diverticulum 84 has been inverted and the bioadhesive 91 has been delivered. For simplicity, the openings and blocking tube (if used) of needle 111 are not shown. However, a needle similar to needle 111 without the openings along the side or the blocking tube can be used.

Prior to breaking off the needle 111, a collapsing device 150 can be advanced along the delivery shaft 74. The collapsing device 150 can include at least two collapsing shafts 152 with projections 154 positioned at the distal end of the collapsing shafts 152. The at least two projections 154 should be diametrically opposed. In one example, at least four collapsing shafts 152 with projections 154 are positioned equidistance around a longitudinal axis of the delivery shaft 75.

The collapsing device 150 is advanced until a distal end 155 of the projections 154 contact an inner surface 79 of the colon 80, as seen in FIG. 26. Once in position, the distance between the projections 154 can be reduced such that the projections 154 contact and collapse the inverted diverticulum 84 including the bioadhesive 91, as seen in FIG. 27. In one example, a closing sheath can be advanced over the collapsing shafts 152 to reduce the distance between the projections 154. However, other mechanisms to reduce the distance between the opposing projections 154 are contemplated. As seen in FIG. 27, the force applied to the diverticulum 84 via the projections 154 can collapse the diverticulum 84 such that the diverticulum 84 adheres to itself and portions of the needle 111. Additionally, in one example, the force is sufficient to deform the arms 118 of the needle 111. In one example, suction applied via the needle 111 can be used in conjunction with the collapsing device 150 to collapse and close the inverted diverticulum 84.

Providing the collapsing device 150 can provide a compression force around the diverticulum and tighten the seal around the inverted diverticulum 84, which assists in maintaining the inverted diverticulum 84 in the closed state. As discussed herein, by closing the inverted diverticulum 84 allows the diverticulum 84 to heal on the serosa side 102 and necrose on the mucosa 104 side, eventually the tissue being absorbed or falling off, while the needle 111 and stent 140 can fall off and be expelled from the patient.

FIGS. 28 and 29 illustrate an additional step to treating the diverticulum. While FIGS. 28 and 29 are shown using needle 111, the methods and devices shown in FIGS. 28 and 29 can be used with any of the methods and devices disclosed herein. As shown in FIG. 28, the diverticulum 84 has been inverted and the bioadhesive 91 has been delivered. For simplicity, the openings and blocking tube (if used) of needle 111 are not shown. However, a needle similar to needle 111 without the openings along the side or the blocking tube can be used.

Prior to breaking off the needle 111, a collapsing device 160 can be advanced from a collapsing shaft 158. The collapsing device 160 can include at least two conduits 162 each defining a lumen 163 that is in fluid communication with a balloon 164 defining a balloon chamber 166.

The balloon 164 can be positioned at an end of the conduit 162. The balloon 164 can be, for example, a flexible, inflatable bladder formed from an elastic material. The balloon 164 may be attached or fused to the conduit 162 at an attachment point 165, or may integrally be formed with the conduit 162 such that the balloon 164 and the conduit 162 form a unitary structure. In one non-limiting example, the conduit 162 and the balloon 164 can be formed from a silicone-containing material, such as silicone rubber, or from a fluoro-rubber. As another non-limiting example, the conduit 162 and the balloon 164 can be formed from polymer material or a thermoplastic material having a high elasticity.

The balloon 164 can have an unexpanded state (see FIG. 28) and an expanded state (see FIG. 29). A fluid, such as air, may be introduced into the balloon chamber 166 through the conduit 162. As the fluid is introduced into the balloon chamber 166, the balloon chamber 166 can transition from the unexpanded state to the expanded state as a wall 124 of the balloon-forming chamber 106 expands outward. The fluid may be introduced into the balloon chamber 166 until the inverted diverticulum 84 is sufficiently closed. For example, the balloon chamber 166 can continue to expand until the inverted diverticulum 84 has collapsed such that the inverted diverticulum 84 is contacting and adhering to portions of itself and portions of the needle 111.

Providing the collapsing device 160 can provide a compression force around the diverticulum and tighten the seal around the inverted diverticulum 84, which assists in maintaining the inverted diverticulum 84 in the closed state. As discussed herein, by closing the inverted diverticulum 84 allows the diverticulum 84 to heal on the serosa side 102 and necrose on the mucosa 104 side, eventually the tissue being absorbed or falling off, while the needle 111 and stent 140 can fall off and be expelled from the patient.

FIGS. 30-31 illustrate another example of closing the inverted diverticulum 84 using needle 170 and a balloon 172. FIG. 30 illustrates the needle 170, similar to needle 60, having inverted the diverticulum 84. Compared to needle 60, after the diverticulum 84 is inverted, instead of advancing conduit 68 from needle 60, a perforated balloon 172 is advanced from needle 170. The perforated balloon 172 is attached to a conduit 175 and can be coupled to the conduit 175 as discussed herein with respect to collapsing device 160. Additionally, the perforated balloon 172 and conduit 175 can be formed from the materials discussed herein for balloon 164 and conduit 162 discussed herein. In FIG. 30, the balloon 172 is at a partially expanded state. The balloon 172 can expand by introducing a fluid into the balloon 172 via the conduit 162. In one example, the fluid is the bioadhesive 91 and the bioadhesive 91 flows through the conduit 175 and into the balloon 172 to expand the balloon 172. The balloon 172 is expanded until an external surface of the balloon 172 contacts an inner surface of the inverted diverticulum 84, as seen in FIG. 31. After contact between the balloon 172 and the inner surface of the inverted diverticulum 84 has been made and the inverted diverticulum 82 is adhered to the balloon 172, the balloon can be deflated by applying suction to the conduit 175 to collapse the balloon 172 and thereby collapse the inverted diverticulum 84. Since the fluid to expand the balloon 172 was the adhesive 91, once the balloon 172 is deflated the inner surfaces of the balloon 172 can stick to each other, thereby maintaining the inverted diverticulum 84 in the closed position, as seen in FIG. 32.

FIG. 33 illustrates another method and device for treating a diverticulum 84. As seen in FIG. 33, the diverticulum 84 has been inverted with a needle 170, similar to needle 60. However, instead of collapsing the inverted diverticulum 84, the band 132 was placed at the base of the inverted diverticulum 84. For example, the band 132 can be placed as described with band 132 in FIGS. 20-22. After the band 132 is placed at the base of the inverted diverticulum 84, a material 171 can be inserted into the diverticulum 84 via a lumen 173 of the needle 170. The material can be the bioadhesive or any material that can either assist or does not interfere with the inverted diverticulum necrosing.

Instead of using needle 170 to invert the diverticulum 84, FIGS. 34-37 illustrate using suction to invert the diverticulum 84. FIG. 34 illustrates advancing a suction device 180 having a lumen 182 into the diverticulum 84 until the suction device 180 contacts an inner surface 81 of the diverticulum 84. Suction can be applied to couple the diverticulum to the suction device 180. The suction device 180 can then be retracted to invert the diverticulum 84, as shown in FIG. 35. After the diverticulum 84 has been inverted, the band 132 can be advanced (see FIG. 36) and moved from the delivery sheath 130 and positioned at the base of the diverticulum 84, as shown in FIG. 37. Once the inverted diverticulum 84 is inverted, the material 186 can be delivered. For example, a needle 184 can be advanced from the suction device 180 and pierce the inverted diverticulum 84 to deliver the material 186.

FIGS. 38-40 illustrate different methods of banding and filling the diverticula 84. For example, FIG. 38 illustrates the inverted diverticula 84 including the band 134. In this example, the diverticula 84 can be inverted by, e.g., but not limited to, a suction device inserted through the colon lumen 24. However, a delivery shaft 190 and needle 192 that is configured to introduce the material 186 can be introduced via a laparoscope. FIG. 39 illustrates banding the diverticula 84 and inserting the material 186 both through the laparoscope. FIG. 40 illustrates banding the diverticulum 84 with a laparoscope and inserting the material 186 into the diverticulum 84 using an endoscope.

VARIOUS NOTES & EXAMPLES

Example 1 can provide a system for treating a diverticulum, comprising: an endoscopic device including a shaft configured to be deployed at a site adjacent to a diverticulum, the shaft having instrument lumen; and a treatment device configured to be inserted into the instrument lumen of the endoscopic device, the treatment device including: a needle having a tip and at least one expandable arm, the needle configured to pierce the diverticulum and the at least one expandable arm configured to engage and invert the diverticulum.

Example 2 can include, or can optionally be combined with the subject matter of Example 1, to optionally include where the treatment device further includes: a conduit positioned within and configured to advance from the needle, wherein a portion of the conduit includes a plurality of openings.

Example 3 can include, or can optionally be combined with the subject matter of one or any combination of Examples 1 or 2 to optionally include where the conduit is reversibly coupled to a pumping device configured to deliver a material to a cavity of the inverted diverticulum and a suction device configured to apply suction to the cavity of the inverted diverticulum.

Example 4 can include, or can optionally be combined with the subject matter of one or any combination of Examples 1 through 3 to optionally include where the material is a bioadhesive.

Example 5 can include, or can optionally be combined with the subject matter of one or any combination of Examples 1 through 4 to optionally include a blocking tube configured to move relative to the conduit and block one or more of the plurality of openings.

Example 6 can include, or can optionally be combined with the subject matter of one or any combination of Examples 1 through 5 to optionally include where the needle further includes a plurality of openings along a body of the needle.

Example 7 can include, or can optionally be combined with the subject matter of one or any combination of Examples 1 through 6 to optionally include a delivery shaft positioned around the needle, the delivery shaft configured to translate relative to the needle, wherein the delivery shaft is configured to be coupled to a suction device to apply suction to an external surface of the inverted diverticulum Example 8 can include, or can optionally be combined with the subject matter of one or any combination of Examples 1 through 7 to optionally include where the at least one expandable arm is formed from a shape memory material.

Example 9 can include, or can optionally be combined with the subject matter of one or any combination of Examples 1 through 8 to optionally include where the at least one expandable arm rotates about a pivot point.

Example 10 can include, or can optionally be combined with the subject matter of one or any combination of Examples 1 through 9 to optionally include wherein the treatment device further includes: an elastic band positioned around a delivery sheath; and at least one pusher configured to move the elastic band from the delivery sheath.

Example 11 can include, or can optionally be combined with the subject matter of one or any combination of Examples 1 through 10 to optionally include wherein the treatment device further includes: a collapsible stent positioned around a delivery sheath; and at least one pusher configured to move the collapsible stent form from the delivery sheath.

Example 12 can include, or can optionally be combined with the subject matter of one or any combination of Examples 1 through 11 to optionally include wherein a portion of the treatment device includes one of: an electrode configured to apply electrosurgical energy to surrounding tissue; a heating device configured to heat surrounding tissue; and a cooling device configured to cool surrounding tissue.

Example 13 can provide a method of treating a diverticulum, the method comprising: placing a working end of an endoscope device within a colonic lumen relative to a diverticulum; advancing a treatment device from the working end and into the diverticulum; inverting the diverticulum with the treatment device; collapsing the inverted diverticulum around a portion of the treatment device; adhering the inverted diverticulum to the portion of the treatment device to maintain the diverticulum in a closed state; and breaking away a portion of the treatment device positioned within the inverted diverticulum.

Example 14 can include, or can optionally be combined with the subject matter of one or any combination of Examples 1 through 13 to optionally include where collapsing the inverted diverticulum includes applying suction to the inverted diverticulum via the treatment device.

Example 15 can include, or can optionally be combined with the subject matter of one or any combination of Examples 1 through 14 to optionally include where adhering the inverted diverticulum to the portion of the treatment device includes inserting a bioadhesive into the inverted diverticulum via the treatment device such that an inner surface of the inverted diverticulum adheres to the portion of the treatment device.

Example 16 can include, or can optionally be combined with the subject matter of one or any combination of Examples 1 through 15 to optionally include applying an elastic band to a base of the inverted diverticulum.

Example 17 can include, or can optionally be combined with the subject matter of one or any combination of Examples 1 through 16 to optionally include positioning a collapsing device around the inverted diverticulum; and activating the collapsing device such that the inverted diverticulum collapses around the treatment device.

Example 18 can provide a treatment device configured to be inserted into an instrument lumen of an endoscopic device, the treatment device including: a needle having a body defining a lumen, the needing extending from a tip at the distal end and having at least one expandable arm, the needle configured to pierce a diverticulum and the at least one expandable arm configured to engage and invert the diverticulum.

Example 19 can include, or can optionally be combined with the subject matter of one or any combination of Examples 1 through 18 to optionally include where the body of the needle includes a plurality of openings, the plurality of openings configured to deliver a bioadhesive to the inverted diverticulum and apply suction to the inverted diverticulum.

Example 20 can include, or can optionally be combined with the subject matter of one or any combination of Examples 1 through 19 to optionally include a conduit positioned within and configured to advance from the needle, wherein a portion of the conduit includes a plurality of openings, the plurality of openings configured to deliver a bioadhesive to the inverted diverticulum and apply suction to the inverted diverticulum Example 21 can provide a method of treating a diverticulum, the method comprising: placing a working end of an endoscope device within a colonic lumen relative to a diverticulum; advancing a treatment device from the working end, the treatment device including: a first member configured to couple to the diverticulum; and a second member positioned within and configured to advance from the first member; advancing the first member until the first member is coupled to the diverticulum; retracting the first member to invert the diverticulum; advancing the second member into the inverted diverticulum; delivering a bioadhesive into the inverted diverticulum via the second member; and collapsing the inverted diverticulum such that the inverted diverticulum is adhered to portion of itself and portions of the treatment device.

Example 22 can include, or can optionally be combined with the subject matter of one or any combination of Examples 1 through 21 to optionally include where the first member of the treatment device includes a needle including a tip and at least one expandable arm.

Example 23 can include, or can optionally be combined with the subject matter of one or any combination of Examples 1 through 22 to optionally include where advancing the first member until the first member is coupled to the diverticulum includes: advancing the needle until the needle pierces the diverticulum and the expandable arm expands to couple the diverticulum to the needle.

Example 24 can include, or can optionally be combined with the subject matter of one or any combination of Examples 1 through 23 to optionally include where the second member of the treatment device includes a conduit having a body portion and a plurality of openings extending along a distal portion of the body portion.

Example 25 can include, or can optionally be combined with the subject matter of one or any combination of Examples 1 through 24 to optionally include where delivering the bioadhesive into the inverted diverticulum includes: pumping the bioadhesive through the conduit, through the plurality of openings, and into the inverted diverticulum.

Example 26 can include, or can optionally be combined with the subject matter of one or any combination of Examples 1 through 25 to optionally include where, after collapsing the inverted diverticulum, the method includes: applying an electrosurgical energy to the inverted diverticulum via the conduit.

Example 27 can include, or can optionally be combined with the subject matter of one or any combination of Examples 1 through 26 to optionally include where the method further includes: advancing a closing device from a delivery sheath to a base of the inverted diverticulum.

Example 28 can include, or can optionally be combined with the subject matter of one or any combination of Examples 1 through 27 to optionally include where the closing device is an elastic band.

Example 29 can include, or can optionally be combined with the subject matter of one or any combination of Examples 1 through 28 to optionally include where the method further includes: positioning a collapsing device around the inverted diverticulum; and activating the collapsing device such that the inverted diverticulum collapses around the treatment device.

Example 30 can include, or can optionally be combined with the subject matter of one or any combination of Examples 1 through 29 to optionally include where, after collapsing the inverted diverticulum, the method includes: breaking off the treatment device such that a portion of the treatment device remains within the inverted diverticulum.

Example 31 can include, or can optionally be combined with the subject matter of one or any combination of Examples 1 through 30 to optionally include wherein, prior to advancing the treatment device, the method further includes at least one of: aspirating the diverticulum utilizing an aspiration device in operable cooperation with the endoscopic device, the aspiration device configured to suction the undesirable material from the at least one diverticulum; and irrigating the at least one diverticulum utilizing an irrigation device in operable cooperation with the endoscopic device, the lavage device configured to utilize fluid to flush out the at least one diverticulum.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system for treating a diverticulum, comprising:
an endoscopic device including a shaft configured to be deployed at a site adjacent to a diverticulum, the shaft including an instrument lumen; and
a treatment device configured to be inserted into the instrument lumen of the endoscopic device, the treatment device including:
a needle including a needle lumen, a tip located at a distal end of the needle, and at least one pliable arm proximate to the needle tip, the at least one pliable arm including an inner side proximate to the needle and an opposing outer side, the needle configured to extend from the instrument lumen and pierce the diverticulum and the at least one pliable arm configured to move to an expanded position to engage and invert the diverticulum;
wherein the at least one pliable arm flexes and deforms to permit engagement of the inner side of the arm with the diverticulum to contribute to inverting the diverticulum.

2. The system of claim 1, wherein the treatment device further includes:
a conduit positioned within and configured to advance from the needle lumen, wherein a portion of the conduit includes a plurality of openings.

3. The system of claim 2, wherein the conduit is reversibly coupled to a pumping device configured to deliver a material to a cavity of the inverted diverticulum and a suction device configured to apply suction to the cavity of the inverted diverticulum.

4. The system of claim 3, wherein the material is a bioadhesive.

5. The system of claim 2, further including:
a blocking tube configured to move relative to the conduit and block one or more of the plurality of openings.

6. The system of claim 1, wherein the needle includes the at least one pliable arm configured to be located along a body of the needle, in an insertion configuration; and
Wherein the at least one pliable arm is configured to flex into a concave form relative to the tip of the needle as the at least one pliable arm inverts the diverticulum.

7. The system of claim 1, wherein the at least one pliable arm is formed from a shape memory material.

8. The system of claim 1, wherein the at least one pliable arm rotates about a pivot point.

9. The system of claim 1, wherein a portion of the treatment device includes one of:
an electrode configured to apply electrosurgical energy to surrounding tissue;
a heating device configured to heat the surrounding tissue; and
a cooling device configured to cool the surrounding tissue.

10. A treatment device configured to be inserted into an instrument lumen of an endoscopic device, the endoscopic device comprising:
a shaft configured to be deployed from the instrument lumen of the endoscopic device, the shaft including a shaft lumen; and
the treatment device configured to extend from the shaft lumen and retract into the shaft lumen including:
a needle including:
a needle body defining a needle lumen, the needle body extending proximally from a needle tip at a distal end of the needle body;
at least one expandable arm proximate to the needle tip, the at least one expandable arm including an inner side proximate to the needle body and an outer side, the at least one expandable arm is configured to flex; and
the needle tip is configured to pierce a diverticulum;
wherein the at least one expandable arm is configured to move away from the needle body to permit the inner side of the at least one expandable arm to flexibly conform to tissue of a treatment site and couple with the diverticulum to contribute to inverting the diverticulum.

11. The treatment device of claim 10, further including:
a conduit positioned within and configured to advance from the needle, wherein a portion of the conduit includes a plurality of openings, the plurality of openings configured to deliver a bioadhesive to the inverted diverticulum and apply suction to the inverted diverticulum.

12. The treatment device of claim 10, including an endoscopic device including a shaft including a working portion along a distal portion of the shaft;
the needle is configured to advance and retract from the lumen;
wherein the shaft does not obstruct inverting the diverticulum.

13. The system for treating a diverticulum of claim 1, wherein the at least one pliable arm is configured to conform to the diverticulum.

14. The system for treating a diverticulum of claim 1, wherein the at least one pliable arm deforms in a concave shape according to the form of the diverticulum.

* * * * *